(12) United States Patent
Zhang et al.

(10) Patent No.: US 12,171,610 B2
(45) Date of Patent: *Dec. 24, 2024

(54) SYSTEMS AND METHODS FOR LUNG NODULE EVALUATION

(71) Applicant: SHANGHAI UNITED IMAGING INTELLIGENCE CO., LTD., Shanghai (CN)

(72) Inventors: Wenhai Zhang, Shanghai (CN); Ying Shao, Shanghai (CN); Yaozong Gao, Shanghai (CN)

(73) Assignee: SHANGHAI UNITED IMAGING INTELLIGENCE CO., LTD., Shanghai (CN)

(*) Notice: Subject to any disclaimer, the term of this patent is extended or adjusted under 35 U.S.C. 154(b) by 34 days.

This patent is subject to a terminal disclaimer.

(21) Appl. No.: 18/157,068

(22) Filed: Jan. 19, 2023

(65) Prior Publication Data

US 2023/0157659 A1  May 25, 2023

Related U.S. Application Data

(63) Continuation of application No. 17/072,180, filed on Oct. 16, 2020, now Pat. No. 11,605,164.

(30) Foreign Application Priority Data

Oct. 22, 2019 (CN) .......................... 201911004977.X
Nov. 15, 2019 (CN) .......................... 201911120244.X
Dec. 27, 2019 (CN) .......................... 201911383262.2

(51) Int. Cl.
*A61B 6/00* (2024.01)
*G06F 18/24* (2023.01)
(Continued)

(52) U.S. Cl.
CPC ............ *A61B 6/5217* (2013.01); *G06F 18/24* (2023.01); *G06T 7/0012* (2013.01); *G06T 7/11* (2017.01);
(Continued)

(58) Field of Classification Search
CPC ........... G06T 11/00; G06T 2207/10048; G06T 2207/10081; G06T 2207/10088;
(Continued)

(56) References Cited

U.S. PATENT DOCUMENTS 11,263,481 B1 * 3/2022 Takeuchi ............. A61B 6/5217
2003/0099387 A1 5/2003 Doi et al.
(Continued)

FOREIGN PATENT DOCUMENTS

CN   101727537 A   6/2010
CN   104751178 A   7/2015
(Continued)

OTHER PUBLICATIONS

Fausto Milletari et al., V-Net: Fully Convolutional Neural Networks for Volumetric Medical Image Segmentation, 2016 Fourth International Conference on 3D Vision (3DV), 2016, 11 pages.
(Continued)

*Primary Examiner* — Manuchehr Rahmjoo
(74) *Attorney, Agent, or Firm* — METIS IP LLC

(57) ABSTRACT

A method for lung nodule evaluation is provided. The method may include obtaining a target image including at least a portion of a lung of a subject. The method may also include segmenting, from the target image, at least one target region each of which corresponds to a lung nodule of the subject. The method may further include generating an evaluation result with respect to the at least one lung nodule based on the at least one target region.

18 Claims, 23 Drawing Sheets

(51) Int. Cl.

| | |
|---|---|
| *G06T 7/00* | (2017.01) |
| *G06T 7/11* | (2017.01) |
| *G06T 11/00* | (2006.01) |
| *G06V 10/26* | (2022.01) |
| *G06V 10/98* | (2022.01) |
| *A61B 5/00* | (2006.01) |
| *A61B 5/055* | (2006.01) |
| *A61B 6/03* | (2006.01) |
| *A61B 8/08* | (2006.01) |
| *A61B 8/12* | (2006.01) |

(52) U.S. Cl.
CPC .............. *G06T 11/00* (2013.01); *G06V 10/26* (2022.01); *G06V 10/987* (2022.01); *A61B 5/0066* (2013.01); *A61B 5/0075* (2013.01); *A61B 5/055* (2013.01); *A61B 6/032* (2013.01); *A61B 6/037* (2013.01); *A61B 6/4417* (2013.01); *A61B 6/4441* (2013.01); *A61B 8/12* (2013.01); *A61B 8/5223* (2013.01); *G06T 2207/30064* (2013.01); *G06T 2210/12* (2013.01)

(58) Field of Classification Search
CPC . G06T 2207/10101; G06T 2207/10104; G06T 2207/10108; G06T 2207/10132; G06T 2207/20072; G06T 2207/20076; G06T 2207/20081; G06T 2207/20084; G06T 2207/20104; G06T 2207/30061; G06T 2207/30064; G06T 2210/12; G06T 7/0012; G06T 7/11; G06V 10/26; G06V 10/987; G06V 2201/031
See application file for complete search history.

(56) References Cited

U.S. PATENT DOCUMENTS

| | | | |
|---|---|---|---|
| 2005/0063579 A1* | 3/2005 | Lee | G06V 10/26 382/131 |
| 2008/0205717 A1* | 8/2008 | Reeves | G06T 11/008 382/128 |
| 2008/0298658 A1 | 12/2008 | Nakashima et al. | |
| 2016/0063721 A1 | 3/2016 | Nakano | |
| 2016/0247303 A1* | 8/2016 | Aoyama | G16H 30/20 |
| 2018/0267507 A1 | 9/2018 | Chen et al. | |
| 2019/0131016 A1* | 5/2019 | Cohen | G16H 70/60 |
| 2019/0139227 A1 | 5/2019 | Wang et al. | |
| 2019/0180860 A1 | 6/2019 | Bronkalla et al. | |
| 2019/0287242 A1 | 9/2019 | Zhang et al. | |
| 2020/0005460 A1 | 1/2020 | Dou et al. | |

FOREIGN PATENT DOCUMENTS

| | | |
|---|---|---|
| CN | 106650830 A | 5/2017 |
| CN | 107247887 A | 10/2017 |
| CN | 107481215 A | 12/2017 |
| CN | 108615237 A | 10/2018 |
| CN | 108629764 A | 10/2018 |
| CN | 109712131 A | 5/2019 |
| CN | 109758136 A | 5/2019 |
| CN | 109816667 A | 5/2019 |
| CN | 110189307 A | 8/2019 |
| CN | 110223775 A | 9/2019 |
| JP | 2009195380 A | 9/2009 |
| WO | 2019200740 | 10/2019 |

OTHER PUBLICATIONS

Lin, Tsungyi et al., Feature Pyramid Networks for Object Detection, 2017 IEEE Conference on Computer Vision and Pattern Recognition (CVPR), 2017, 9 pages.

Wei, Huamin et al., Pulmonary Nodule Treatment Based on "Phlegm and Blood Stasis" and "Kenang" Theory, World Chinese Medicine, 13(11): 2701-2705, 2708, 2018.

Guo, Wei et al., Discrimination of Benign and Malignant Pulmonary Nodules Based on Multi-dimensional Features, Journal of Shenyang Aerospace University, 33(3): 67-72, 2016.

Pei, Xiaomin, Researches on Key Technologies of Computer Aided Diagnosis for Solitary Pulmonary Nodule Based on CT Images, Dissertation in Biomedical Engineering of Northeastern University, 2011, 124 pages.

Janne Näppi et al., Effect of Knowledge-Guided Colon Segmentation in Automated Detection of Polyps in CT 4 Colonography, Proceedings of SPIE, 4683: 222-229, 2002.

Li, Xing et al., Value of 320-row CT Perfusion Imaging in Differential Diagnosis of Benign and Malignant Pulmonary Nodules, Imaging Research and Medical Applications, 2018, 3 pages.

Jason L. Causey et al., Highly Accurate Model for Prediction of Lung Nodule Malignancy with CT Scans, Scientific Reports, 2018, 12 pages.

* cited by examiner

800

SYSTEMS AND METHODS FOR LUNG NODULE EVALUATION

CROSS-REFERENCE TO RELATED APPLICATIONS

This application is a continuation of U.S. patent application Ser. No. 17/072,180, filed on Oct. 16, 2020, which claims priority to Chinese Patent Application No. 201911004977.X, filed on Oct. 22, 2019, Chinese Patent Application No. 201911120244.2, filed on Nov. 15, 2019, and Chinese Patent Application No. 201911383262.X, filed on Dec. 27, 2019, the contents of each of which are hereby incorporated by reference.

TECHNICAL FIELD

The present disclosure generally relates to image processing, and more particularly, methods and systems for lung nodule evaluation via image processing.

BACKGROUND

A lung nodule is a small growth on a lung and can be benign or malignant. An accurate detection and evaluation of lung nodules are vital for the detection and prevention of lung diseases (e.g., a lung cancer).

SUMMARY

According to an aspect of the present disclosure, a system for lung nodule evaluation may be provided. The system may include one or more storage devices and one or more processors configured to communicate with the one or more storage devices. The one or more storage devices may include a set of instructions. When the one or more processors execute the set of instructions, the one or more processors may be directed to cause the system to perform one or more of the following operations. The system may obtain a target image including at least a portion of a lung of a subject. The system may also segment at least one target region each of which corresponds to a lung nodule of the subject from the target image. The system may further generate an evaluation result with respect to the at least one lung nodule based on the at least one target region.

In some embodiments, to generate an evaluation result with respect to the at least one lung nodule based on the at least one target region, the system may generate a first segmentation image and a second segmentation image based on the target image. The first segmentation image may indicate the left lung and the right lung of the subject segmented from the target image. The second segmentation image may indicate at least one lung lobe of the subject segmented from the target image. For each of the at least one lung nodule, the system may further determine a classification relating to a position of the lung nodule based on the first segmentation image, the second segmentation image, and the target region corresponding to the lung nodule.

In some embodiments, to generate a first segmentation image and a second segmentation image based on the target image, the system may generate the first segmentation image by processing the target image using a lung segmentation model.

In some embodiments, to generate a first segmentation image and a second segmentation image based on the target image, the system may generate the second segmentation image by processing the target image using a lung lobe segmentation model.

In some embodiments, to determine a classification relating to a position of the lung nodule, the system may perform one or more of the following operations. For each of the at least one lung nodule, the system may determine whether the lung nodule is a pleural nodule or a non-pleural nodule based on the first segmentation image and the target region corresponding to the lung nodule.

In some embodiments, to determine whether the lung nodule is a pleural nodule or a non-pleural nodule based on the first segmentation image and the target region corresponding to the lung nodule, the system may determine whether the lung nodule is a candidate pleural nodule or a non-pleural nodule based on the first segmentation image and the target region corresponding to the lung nodule. In response to determining that the lung nodule is a candidate pleural nodule, the system may verify whether the lung nodule is a pleural nodule or a non-pleural nodule based on the first segmentation image and the target region using a pleural nodule identification model.

In some embodiments, for each of the at least one lung nodule, the corresponding target region may be annotated in the target image by a bounding box. To determine whether the lung nodule is a candidate pleural nodule or a non-pleural nodule based on the first segmentation image and the target region corresponding to the lung nodule, the system may generate a transformed bounding box by transforming the bounding box that annotates the target region. The system may also segment a region corresponding to the transformed bounding box from the first segmentation image. The system may further determine whether the lung nodule is a candidate pleural nodule or a non-pleural nodule based on the segmented region.

In some embodiments, the pleural nodule identification model may be generated according to a model training process. To generate the pleural nodule identification model, the system may perform one or more of the following operations. The system may obtain at least one training sample each of which includes a sample first segmentation image of a sample subject, a sample image of a sample lung nodule of the sample subject, and a classification of the sample lung nodule. The sample first segmentation image may indicate the left lung and the right lung of the sample subject. The classification may indicate whether the sample lung nodule is a pleural nodule or not. The system may further generate the pleural nodule identification model by training a preliminary model using the at least one training sample.

In some embodiments, to determine a classification relating to a position of the lung nodule, the system may perform one or more of the following operations. For each of the at least one lung nodule, in response to determining that the lung nodule is a non-pleural nodule, the system may determine whether the lung nodule is a perifissural nodule or a non-perifissural nodule based on the second segmentation image and the target region corresponding to the lung nodule.

In some embodiments, to determine whether the lung nodule is a perifissural nodule or a non-perifissural nodule, the system may determine whether the lung nodule is a candidate perifissural nodule or a non-perifissural nodule based on the second segmentation image and the target region corresponding to the lung nodule. In response to determining that the lung nodule is a candidate perifissural nodule, the system may verify whether the lung nodule is a perifissural nodule or a non-perifissural nodule based on the second segmentation image and the target region using a perifissural nodule identification model.

In some embodiments, for each of the at least one lung nodule, the corresponding target region may be annotated in the target image by a bounding box. To determine whether the lung nodule is a candidate perifissural nodule or a non-perifissural nodule based on the second segmentation image and the target region corresponding to the lung nodule, the system may generate a transformed bounding box by transforming the bounding box. The system may also segment a region corresponding to the transformed bounding box from the second segmentation image. The system may further determine whether the lung nodule is a candidate perifissural nodule or a non-perifissural nodule based on the segmented region.

In some embodiments, the perifissural nodule identification model may be trained according to a training process. To train the perifissural nodule identification model, the system may perform one or more of the following operations. The system may obtain at least one training sample each of which includes a sample second segmentation image of a sample subject, a sample image of a sample lung nodule of the sample subject, and a classification of the sample lung nodule. The sample second segmentation image may indicate at least one lung lobe of the sample subject. The classification may indicate whether the sample lung nodule is a perifissural nodule or not. The system may further generate the perifissural nodule identification model by training a preliminary model using the at least one training sample.

In some embodiments, to determine a classification relating to a position of the lung nodule, the system may perform one or more of the following operations. for each of the at least one lung nodule, in response to determining that the lung nodule is a non-perifissural nodule, the system may determine that the lung nodule is an intrathoracic nodule.

In some embodiments, each of the at least one target region may include 3-dimensional image data. To generate an evaluation result with respect to the at least one lung nodule based on the at least one target region, the system may perform one or more of the following operations. For each of the at least one lung nodule, the system may identify at least one first transverse section of the target region corresponding to the lung nodule. The system may further determine a Hounsfield unit (HU) value of the lung nodule based on the at least one first transverse section of the target region corresponding to the lung nodule.

In some embodiments, to determine a HU value of the lung nodule based on the at least one first transverse section of the target region of the lung nodule, the system may perform one or more of the following operations. For each of the at least one first transverse section, the system may generate a second transverse section by performing an edge removal operation on the first transverse section. The system may also generate a target transverse section based on the first transverse section and the second transverse section. The system may also determine a HU value of the target transverse section. The system may further determine the HU value of the lung nodule based on the HU value of the at least one target transverse section.

In some embodiments, to generate a target transverse section based on the first transverse section and the second transverse section, the system may determine a ratio of a size of the second transverse section to a size of the first transverse section. The system may also generate a comparison result by comparing the ratio with a first threshold and a second threshold, the second threshold being greater than the first threshold. The system may further generate the target transverse section based on the comparison result, and one of the first transverse section and the second transverse section.

In some embodiments, the comparison result may include that the ratio is smaller than the first threshold, and the generating the target transverse section may comprise designating the first transverse section as the target transverse section. The comparison result may also include that the ratio is greater than the first threshold and smaller than the second threshold, and the generating the target transverse section may comprise designating the second transverse section as the target transverse section. The comparison result may further include that the ratio is greater than the second threshold, and the generating the target transverse section may comprise generating the target transverse section by performing an edge removal operation on the second transverse section.

In some embodiments, to identify at least one first transverse section of the target region corresponding to the lung nodule, the system may identify a plurality of candidate transverse sections of the target region. The system may also determine an area of each of the plurality of candidate transverse sections of the target region. The system may also select a first candidate transverse section that has the largest area among the plurality of candidate transverse sections. The system may further designate the first candidate transverse section as one of the at least one first transverse section.

In some embodiments, to identify at least one first transverse section of the target region corresponding to the lung nodule, the system may select one or more second candidate transverse sections each of which within a predetermined distance with respect to the first candidate transverse section among the plurality of candidate transverse sections. The system may further designate each of the one or more second candidate transverse sections as one of the at least one first transverse section.

In some embodiments, to generate an evaluation result with respect to the at least one lung nodule based on the at least one target region, the system may perform one or more of the following operations. For each of the at least one lung nodule, the system may determine a malignancy degree of the lung nodule based on the target region corresponding to the lung nodule.

In some embodiments, to determine a malignancy degree of the lung nodule based on the target region corresponding to the lung nodule, the system may perform one or more of the following operations. For each of the at least one lung nodule, the system may determine size information of the lung nodule based on the target region. The system may also determine symptom information of the lung nodule based on the target region. The system may further determine the malignancy degree of the lung nodule based on the size information and the symptom information.

In some embodiments, the symptom information may be determined based on the target region using a symptom determination model.

In some embodiments, to determine a malignancy degree of the lung nodule based on the target region corresponding to the lung nodule, the system may determine density information of the lung nodule based on the target region. The malignancy degree of the lung nodule may be further determined based further on the density information of the lung nodule.

In some embodiments, the density information of the lung nodule may be determined based on the target region using a density determination model.

In some embodiments, to determine a malignancy degree of the lung nodule based on the target region corresponding to the lung nodule, the system may determine position information of the lung nodule based on the target region. The malignancy degree of the lung nodule may be further determined based on the size information, the symptom information, and the position information of the lung nodule.

In some embodiments, to determine a malignancy degree of the lung nodule based on the target region corresponding to the lung nodule, the system may obtain clinical information relating to the lung nodule. The malignancy degree of the lung nodule may be further determined based on the size information, the symptom information, the position information, and the clinical information of the lung nodule.

In some embodiments, to determine the malignancy degree of the lung nodule based on the size information, the symptom information, the position information, and the clinical information of the lung nodule, the system may determine a probability that the lung nodule is malignant based on the size information, the symptom information, the position information, and the clinical information of the lung nodule. The system may further determine the malignancy degree of the lung nodule based on the probability.

According to another aspect of the present disclosure, a method for lung nodule evaluation may be provided. The method may include obtaining a target image including at least a portion of a lung of a subject. The method may also include segmenting at least one target region each of which corresponds to a lung nodule of the subject from the target image. The method may further include generating an evaluation result with respect to the at least one lung nodule based on the at least one target region.

According to yet another aspect of the present disclosure, a non-transitory computer readable medium may be provided. The non-transitory computer readable may include at least one set of instructions for lung nodule evaluation. When executed by one or more processors of a computing device, the at least one set of instructions may cause the computing device to perform a method. The method may include obtaining a target image including at least a portion of a lung of a subject. The method may also include segmenting at least one target region each of which corresponds to a lung nodule of the subject from the target image. The method may further include generating an evaluation result with respect to the at least one lung nodule based on the at least one target region.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

Figure 2:
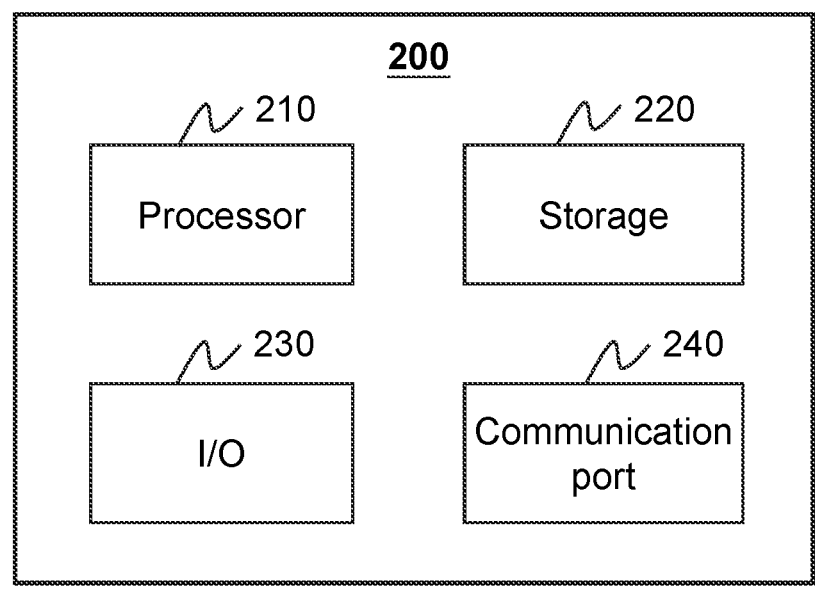
FIG. 2 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image. An anatomical structure shown in an image of a subject may correspond to an actual anatomical structure existing in or on the subject's body. The term "segmenting an anatomical structure" or "identifying an anatomical structure" in an image of a subject may refer to segmenting or identifying a portion in the image that corresponds to an actual anatomical structure existing in or on the subject's body.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and methods for non-invasive biomedical imaging, such as for disease diagnostic or research purposes. In some embodiments, the systems may include a single modality imaging system and/or a multi-modality imaging system. The single modality imaging system may include, for example, an ultrasound imaging system, an X-ray imaging system, an computed tomography (CT) system, a magnetic resonance imaging (MRI) system, an ultrasonography system, a positron emission tomography (PET) system, an optical coherence tomography (OCT) imaging system, an ultrasound (US) imaging system, an intravascular ultrasound (IVUS) imaging system, a near-infrared spectroscopy (NIRS) imaging system, a far-infrared (FIR) imaging system, or the like, or any combination thereof. The multi-modality imaging system may include, for example, an X-ray imaging-magnetic resonance imaging (X-ray-MRI) system, a positron emission tomography-X-ray imaging (PET-X-ray) system, a single-photon emission computed tomography-magnetic resonance imaging (SPECT-MRI) system, a positron emission tomography-computed tomography (PET-CT) system, a C-arm system, a digital subtraction angiography-magnetic resonance imaging (DSA-MRI) system, etc. It should be noted that the imaging system described below is merely provided for illustration purposes, and not intended to limit the scope of the present disclosure.

The term "imaging modality" or "modality" as used herein broadly refers to an imaging method or technology that gathers, generates, processes, and/or analyzes imaging information of a subject. The subject may include a biological subject and/or a non-biological subject. The biological subject may be a human being, an animal, a plant, or a portion thereof (e.g., a heart, a breast, etc.). In some embodiments, the subject may be a man-made composition of organic and/or inorganic matters that are with or without life.

An accurate detection and evaluation of lung nodules are vital for the detection and prevention of lung diseases (e.g., a lung cancer). For example, the evaluation of a lung nodule may involve determining one or more qualitative or quantitative parameters, such as a position classification, a HU value, and/or a malignancy degree of the lung nodule. Conventionally, a user (e.g., a doctor) may need to identify a lung nodule from image data of a lung, and determine an evaluation result of the lung nodule (e.g., the position and/or the malignant degree of the lung nodule) according to experience. However, such evaluation of the lung nodule may be inefficient and/or susceptible to human errors or subjectivity. Thus, it may be desirable to develop systems and methods for automated evaluation of a lung nodule, thereby improving the evaluation efficiency and/or accuracy. The terms "automatic" and "automated" are used interchangeably referring to methods and systems that analyze information and generates results with little or no direct human intervention.

An aspect of the present disclosure relates to systems and methods for lung nodule evaluation. The systems may obtain a target image including at least a portion of a lung of a subject. The systems may segment, from the target image, at least one target region each of which corresponds to a lung nodule of the subject. The systems may further generate an evaluation result with respect to the at least one lung nodule based on the at least one target region. The evaluation result of the at least one lung nodule may include, for example, a position classification, a HU value, and/or a malignancy degree of each lung nodule. Compared with a conventional lung nodule evaluation approach which involves a lot of human intervention, the systems and methods of the present disclosure may be implemented with reduced or minimal or without user intervention, which is more efficient and accurate by, e.g., reducing the workload of a user, cross-user variations, and the time needed for the lung nodule evaluation. In addition, in some embodiments, various parameters of a lung nodule may be determined, thereby achieving a comprehensive and accurate evaluation of the lung nodule.

Moreover, in some embodiments, the evaluation of a lung nodule may be implemented based on one or more machine learning models (e.g., deep learning models). Merely by way of example, one or more of a lung nodule segmentation model, a lung segmentation model, a lung lobe segmentation model, a pleural nodule identification model, a perifissural nodule identification model, a symptom determination model, and a density determination model may be utilized in the evaluation of the lung nodule. The utilization of the machine learning model(s) may further improve the accuracy and/or efficiency of the lung nodule evaluation.

Figure 1:
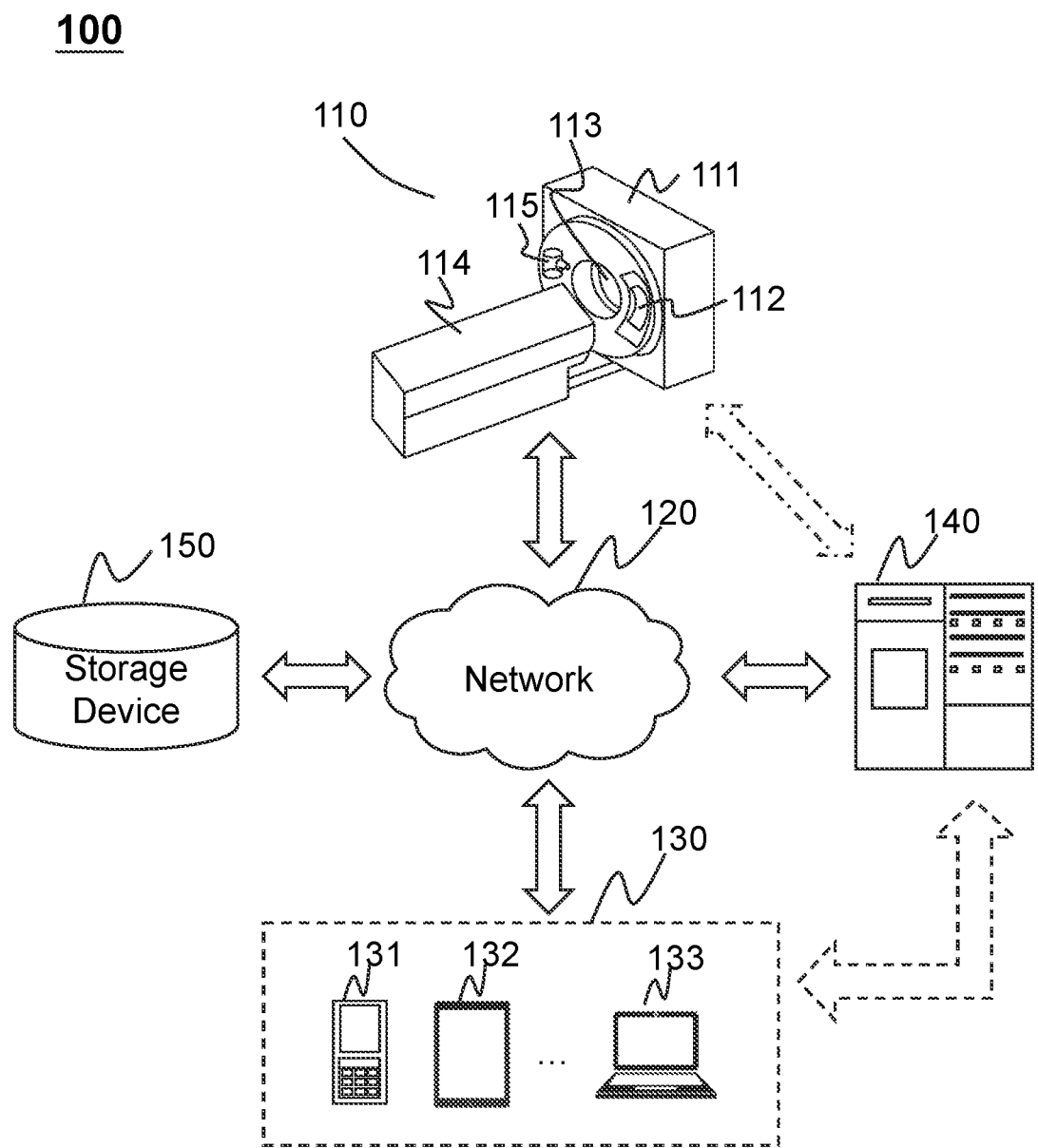
FIG. 1 is a schematic diagram illustrating an exemplary imaging system according to some embodiments of the present disclosure.

FIG. 1 is a schematic diagram illustrating an exemplary imaging system 100 according to some embodiments of the present disclosure. As shown, the imaging system 100 may include an imaging device 110, a network 120, one or more terminals 130, a processing device 140, and a storage device 150. In some embodiments, the imaging device 110, the terminal(s) 130, the processing device 140, and/or the storage device 150 may be connected to and/or communicate with each other via a wireless connection (e.g., the network 120), a wired connection, or a combination thereof. The connection between the components of the imaging system 100 may be variable. Merely by way of example, the imaging device 110 may be connected to the processing device 140 through the network 120, as illustrated in FIG. 1. As another example, the imaging device 110 may be connected to the processing device 140 directly or through the network 120. As a further example, the storage device 150 may be connected to the processing device 140 through the network 120 or directly.

The imaging device 110 may generate or provide image data related to a subject via scanning the subject. In some embodiments, the subject may include a biological subject and/or a non-biological subject. For example, the subject may include a specific portion of a body, such as a heart, a breast, or the like. In some embodiments, the imaging device 110 may include a single-modality scanner (e.g., an MRI device, a CT scanner) and/or multi-modality scanner (e.g., a PET-MRI scanner) as described elsewhere in this disclosure. In some embodiments, the image data relating to the subject may include projection data, one or more images of the subject, etc. The projection data may include raw data generated by the imaging device 110 by scanning the subject and/or data generated by a forward projection on an image of the subject.

In some embodiments, the imaging device 110 may include a gantry 111, a detector 112, a detecting region 113, a scanning table 114, and a radioactive scanning source 115. The gantry 111 may support the detector 112 and the radioactive scanning source 115. The subject may be placed on the scanning table 114 to be scanned. The radioactive scanning source 115 may emit radioactive rays to the subject. The radiation may include a particle ray, a photon ray, or the like, or a combination thereof. In some embodiments, the radiation may include a plurality of radiation particles (e.g., neutrons, protons, electron, μ-mesons, heavy ions), a plurality of radiation photons (e.g., X-ray, a γ-ray, ultraviolet, laser), or the like, or a combination thereof. The detector 112 may detect radiations and/or radiation events (e.g., gamma photons) emitted from the detecting region 113. In some embodiments, the detector 112 may include a plurality of detector units. The detector units may include a scintillation detector (e.g., a cesium iodide detector) or a gas detector. The detector unit may be a single-row detector or a multi-rows detector.

The network 120 may include any suitable network that can facilitate the exchange of information and/or data for the imaging system 100. In some embodiments, one or more components of the imaging system 100 (e.g., the imaging device 110, the processing device 140, the storage device 150, the terminal(s) 130) may communicate information and/or data with one or more other components of the imaging system 100 via the network 120. For example, the processing device 140 may obtain image data from the imaging device 110 via the network 120. As another example, the processing device 140 may obtain user instruction(s) from the terminal(s) 130 via the network 120.

The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The terminal(s) 130 may be connected to and/or communicate with the imaging device 110, the processing device 140, and/or the storage device 150. For example, the terminal(s) 130 may receive a user instruction to evaluate a lung nodule of the subject. As another example, the terminal(s) 130 may display an evaluation result of the lung nodule of the subject generated by the processing device 140. In some embodiments, the terminal(s) 130 may include a mobile device 131, a tablet computer 132, a laptop computer 133, or the like, or any combination thereof. For example, the mobile device 131 may include a mobile phone, a personal digital assistant (PDA), a gaming device, a navigation device, a point of sale (POS) device, a laptop, a tablet computer, a desktop, or the like, or any combination thereof. In some embodiments, the terminal(s) 130 may include an input device, an output device, etc. In some embodiments, the terminal(s) 130 may be part of the processing device 140.

The processing device 140 may process data and/or information obtained from the imaging device 110, the storage device 150, the terminal(s) 130, or other components of the imaging system 100. In some embodiments, the processing device 140 may be a single server or a server group. The server group may be centralized or distributed. For example, the processing device 140 may generate one or more models that can be used in the evaluation of a lung nodule. As another example, the processing device 140 may apply the model(s) in the evaluation of a lung nodule. In some embodiments, the model(s) may be generated by a processing device, while the application of the model(s) may be performed on a different processing device. In some embodiments, the model(s) may be generated by a processing device of a system different from the imaging system 100 or a server different from the processing device 140 on which the application of the model(s) is performed. For instance, the model(s) may be generated by a first system of a vendor who provides and/or maintains such a model(s), while the lung nodule evaluation may be performed on a second system of a client of the vendor. In some embodiments, the application of the model(s) may be performed online in response to a request for evaluating a lung nodule. In some embodiments, the model(s) may be generated offline.

In some embodiments, the model(s) may be generated and/or updated (or maintained) by, e.g., the manufacturer of the imaging device 110 or a vendor. For instance, the manufacturer or the vendor may load the model(s) into the imaging system 100 or a portion thereof (e.g., the processing device 140) before or during the installation of the imaging device 110 and/or the processing device 140, and maintain or update the model(s) from time to time (periodically or not). The maintenance or update may be achieved by installing a program stored on a storage device (e.g., a compact disc, a USB drive, etc.) or retrieved from an external source (e.g., a server maintained by the manufacturer or vendor) via the network 120. The program may include a new model (e.g., a new model(s)) or a portion of a model that substitute or supplement a corresponding portion of the model.

In some embodiments, the processing device 140 may be local to or remote from the imaging system 100. For example, the processing device 140 may access information and/or data from the imaging device 110, the storage device 150, and/or the terminal(s) 130 via the network 120. As another example, the processing device 140 may be directly connected to the imaging device 110, the terminal(s) 130, and/or the storage device 150 to access information and/or data. In some embodiments, the processing device 140 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 140 may be implemented by a computing device 200 having one or more components as described in connection with FIG. 2.

In some embodiments, the processing device 140 may include one or more processors (e.g., single-core processor(s) or multi-core processor(s)). Merely by way of example, the processing device 140 may include a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction-set computer (RISC), a microprocessor, or the like, or any combination thereof.

The storage device 150 may store data, instructions, and/or any other information. In some embodiments, the storage device 150 may store data obtained from the processing device 140, the terminal(s) 130, and/or the imaging device 110. For example, the storage device 150 may store image data collected by the imaging device 110. As another example, the storage device 130 may store one or more images. As further another example, the storage device 130 may store an evaluation result with respect to a lung nodule. In some embodiments, the storage device 150 may store data and/or instructions that the processing device 140 may execute or use to perform exemplary methods described in the present disclosure. For example, the storage device 150 may store data and/or instructions that the processing device 140 may execute or use for lung nodule evaluation.

In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform as described elsewhere in the disclosure.

In some embodiments, the storage device 150 may be connected to the network 120 to communicate with one or more other components of the imaging system 100 (e.g., the processing device 140, the terminal(s) 130). One or more components of the imaging system 100 may access the data or instructions stored in the storage device 150 via the network 120. In some embodiments, the storage device 150 may be part of the processing device 140.

It should be noted that the above description of the imaging system 100 is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the imaging system 100 may include one or more additional components. Additionally or alternatively, one or more components of the imaging system 100 described above may be omitted. As another example, two or more components of the imaging system 100 may be integrated into a single component.

FIG. 2 is a schematic diagram illustrating exemplary hardware and/or software components of a computing device 200 according to some embodiments of the present disclosure. The computing device 200 may be used to implement any component of the imaging system 100 as described herein. For example, the processing device 140 and/or the terminal(s) 130 may be implemented on the computing device 200, respectively, via its hardware, software program, firmware, or a combination thereof. Although only one such computing device is shown, for convenience, the computer functions relating to the imaging system 100 as described herein may be implemented in a distributed fashion on a number of similar platforms, to distribute the processing load. As illustrated in FIG. 2, the computing device 200 may include a processor 210, a storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process image data obtained from the imaging device 110, the terminal(s) 130, the storage device 150, and/or any other component of the imaging system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the imaging device 110, the terminal(s) 130, the storage device 150, and/or any other component of the imaging system 100. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure.

The I/O 230 may input and/or output signals, data, information, etc. In some embodiments, the I/O 230 may enable a user interaction with the processing device 140. In some embodiments, the I/O 230 may include an input device and an output device. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to another component (e.g., the processing device 140) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 240 may be connected to a network (e.g., the network 120) to facilitate data communications. The communication port 240 may establish connections between the processing device 140 and the imaging device 110, the terminal(s) 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
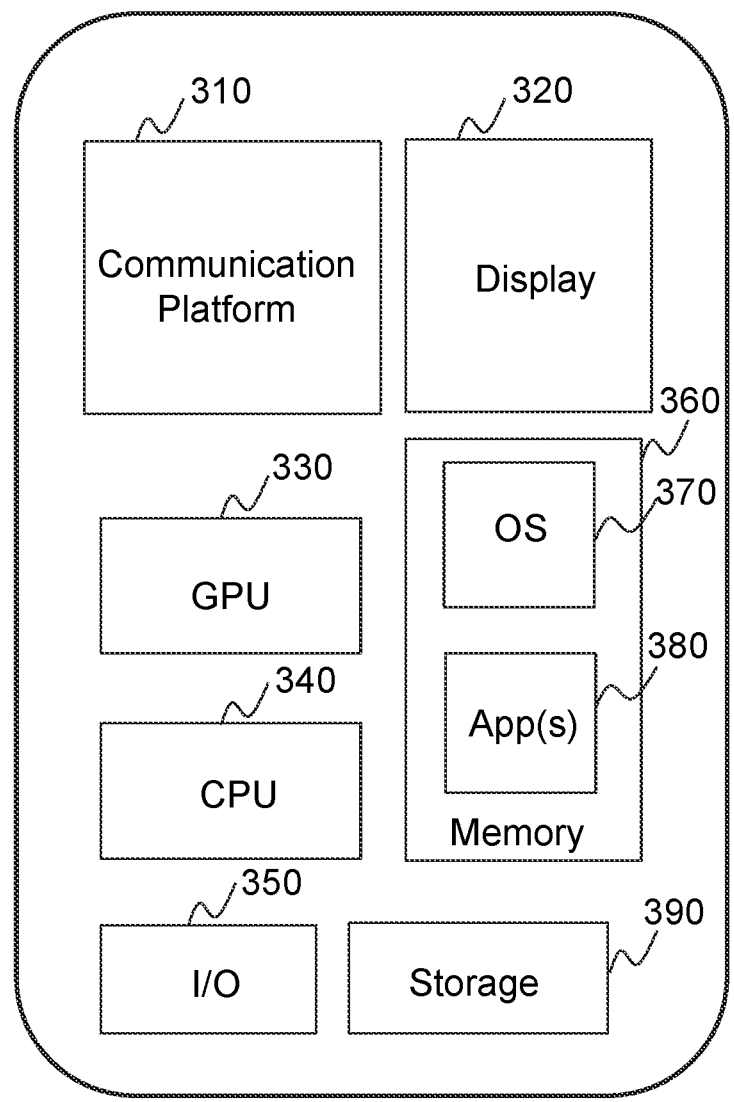
FIG. 3 is a schematic diagram illustrating exemplary hardware and/or software components of a mobile device according to some embodiments of the present disclosure.

FIG. 3 is a schematic diagram illustrating exemplary hardware and/or software components of a mobile device 300 according to some embodiments of the present disclosure. In some embodiments, one or more components (e.g., a terminal 130 and/or the processing device 140) of the imaging system 100 may be implemented on the mobile device 300.

As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the imaging system 100 via the network 120. To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4A:
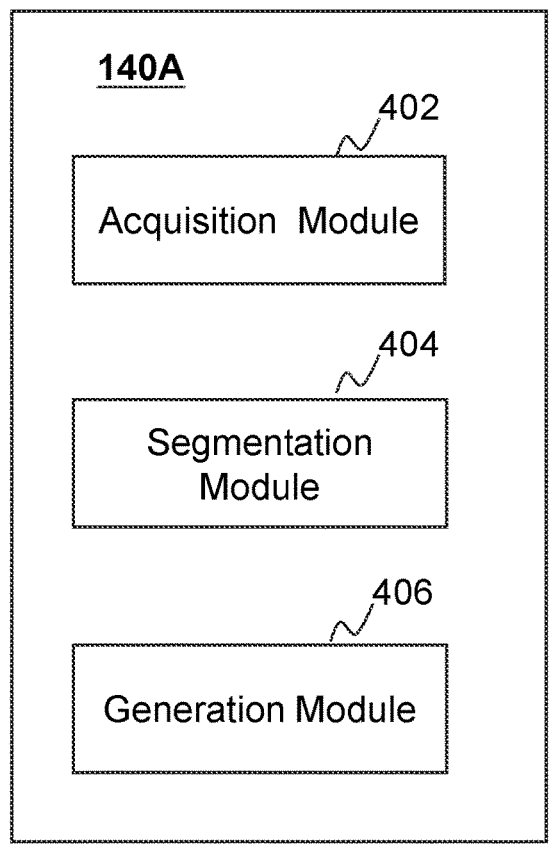
FIGS. 4A and 4B are block diagrams illustrating exemplary processing devices according to some embodiments of the present disclosure.
Figure 4B:
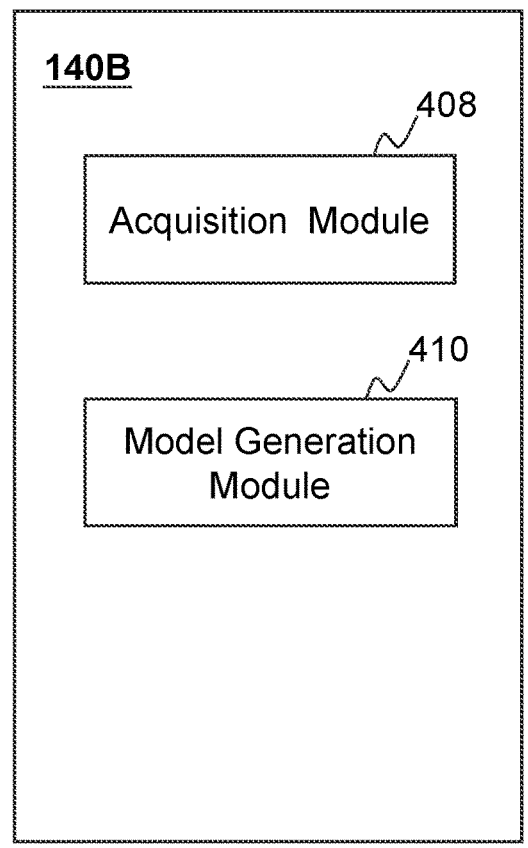

FIGS. 4A and 4B are block diagrams illustrating exemplary processing devices 140A and 140B according to some embodiments of the present disclosure. The processing devices 140A and 140B may be exemplary processing devices 140 as described in connection with FIG. 1. In some embodiments, the processing device 140A may be configured to apply one or more machine learning models in generating an evaluation result with respect to the at least one lung nodule. The processing device 140B may be configured to generate the one or more machine learning models. In some embodiments, the processing devices 140A and 140B may be respectively implemented on a processing unit (e.g., a processor 210 illustrated in FIG. 2 or a CPU 340 as illustrated in FIG. 3). Merely by way of example, the processing devices 140A may be implemented on a CPU 340 of a terminal device, and the processing device 140B may be implemented on a computing device 200. Alternatively, the processing devices 140A and 140B may be implemented on a same computing device 200 or a same CPU 340. For example, the processing devices 140A and 140B may be implemented on a same computing device 200.

As shown in FIG. 4A, the processing device 140A may include an acquisition module 402, a segmentation module 404, and a generation module 406.

The acquisition module 402 may be configured to obtain information relating to the imaging system 100. For example, the acquisition module 402 may obtain a target image including at least a portion of a lung of a subject. The target image may include a 2D image (e.g., a slice image), a 3D image, a 4D image (e.g., a series of 3D images over time), and/or any related image data (e.g., scan data, projection data), or the like. More descriptions regarding the obtaining of the target image including at least a portion of a lung of a subject may be found elsewhere in the present disclosure. See, e.g., operation 502 in FIG. 5 and relevant descriptions thereof.

The segmentation module 404 may be configured to segment at least one target region each of which corresponds to a lung nodule of the subject from the target image. A target region corresponding to a lung nodule may be a region segmented from or identified in the target image that encloses the lung nodule. For example, the target region may include a bounding box enclosing the lung nodule. The bounding box may be 2-dimensional or 3-dimensional. More descriptions regarding the segmentation of the at least one target region each of which corresponds to a lung nodule of the subject from the target image may be found elsewhere in the present disclosure. See, e.g., operation 504 in FIG. 5 and relevant descriptions thereof.

The generation module 406 may be configured to generate an evaluation result with respect to the at least one lung nodule based on the at least one target region. The evaluation result of a lung nodule may include one or more qualitative or quantitative parameters of the lung nodule. For example, the evaluation result of a lung nodule may include a position classification, a HU value, and/or a malignancy degree of the lung nodule.

In some embodiments, the generation module 406 may be configured to determine a classification relating to the position of the lung nodule. For example, based on the position of the lung nodule, the lung nodule may be classified as a pleural nodule, a non-pleural nodule, a perifissural nodule, a non-perifissural nodule, an intrapulmonary nodule, a lung nodule located at the left lung, a lung nodule located at the right lung, or the like, or any combination thereof. More descriptions for the determination of a classification relating to the position of a lung nodule may be found elsewhere in the present disclosure (e.g., operation 508 in FIG. 5, FIGS. 6-17, and the descriptions thereof).

In some embodiments, the generation module 406 may be configured to determine a Hounsfield unit (HU) value of the lung nodule. A HU value of the lung nodule may be determined as a quantitative measurement for measuring X-ray attenuation during the scan of the subject. More descriptions for the determination of a HU value of a lung nodule may be found elsewhere in the present disclosure (e.g., operation 510 in FIG. 5, FIGS. 18-21, and the descriptions thereof).

In some embodiments, the generation module 406 may be configured to determine a malignancy degree of the lung nodule. As used herein, the malignancy degree of a lung nodule may reflect a probability that the lung nodule is malignant (e.g., a malignant cancer). In some embodiments, the malignant degree of the lung nodule may be represented in various forms. For example, the malignant degree may be represented as a score, and a greater score may indicate a higher probability that the lung nodule is malignant. As another example, the malignant degree may include a low-risk degree, a moderate-risk degree, and a high-risk degree. More descriptions for the determination of a malignancy degree of a lung nodule may be found elsewhere in the present disclosure (e.g., operation 512 in FIG. 5, FIGS. 22-23, and the descriptions thereof).

As shown in FIG. 4B, the processing device 140B may include an acquisition module 408 and a model generation module 410.

The acquisition module 408 may be configured to obtain one or more training samples and a corresponding preliminary model. More descriptions regarding the acquisition of the training samples and the corresponding preliminary model may be found elsewhere in the present disclosure. See, e.g., operation 504 in FIG. 5, operation 602 in FIG. 6, operation 604 in FIG. 6, operation 804 in FIG. 8, operation 1004 in FIG. 1000, and relevant descriptions thereof.

The model generation module 410 may be configured to generate the one or more machine learning models by training a preliminary model using the more training samples. In some embodiments, the one or more machine learning models may be generated according to a machine learning algorithm. The machine learning algorithm may include but not be limited to an artificial neural network algorithm, a deep learning algorithm, a decision tree algorithm, an association rule algorithm, an inductive logic programming algorithm, a support vector machine algorithm, a clustering algorithm, a Bayesian network algorithm, a reinforcement learning algorithm, a representation learning algorithm, a similarity and metric learning algorithm, a sparse dictionary learning algorithm, a genetic algorithm, a rule-based machine learning algorithm, or the like, or any combination thereof. The machine learning algorithm used to generate the one or more machine learning models may be a supervised learning algorithm, a semi-supervised learning algorithm, an unsupervised learning algorithm, or the like. More descriptions regarding the generation of the one or more machine learning models may be found elsewhere in the present disclosure. See, e.g., operation 504 in FIG. 5, operation 602 in FIG. 6, operation 604 in FIG. 6, operation 804 in FIG. 8, operation 1004 in FIG. 1000, and relevant descriptions thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 140A and/or the processing device 140B may share two or more of the modules, and any one of the modules may be divided into two or more units. For instance, the processing devices 140A and 140B may share a same acquisition module; that is, the acquisition module 402 and the acquisition module 408 are a same module. In some embodiments, the processing device 140A and/or the processing device 140B may include one or more additional modules, such as a storage module (not shown) for storing data. In some embodiments, the processing device 140A and the processing device 140B may be integrated into one processing device 140.

Figure 5:
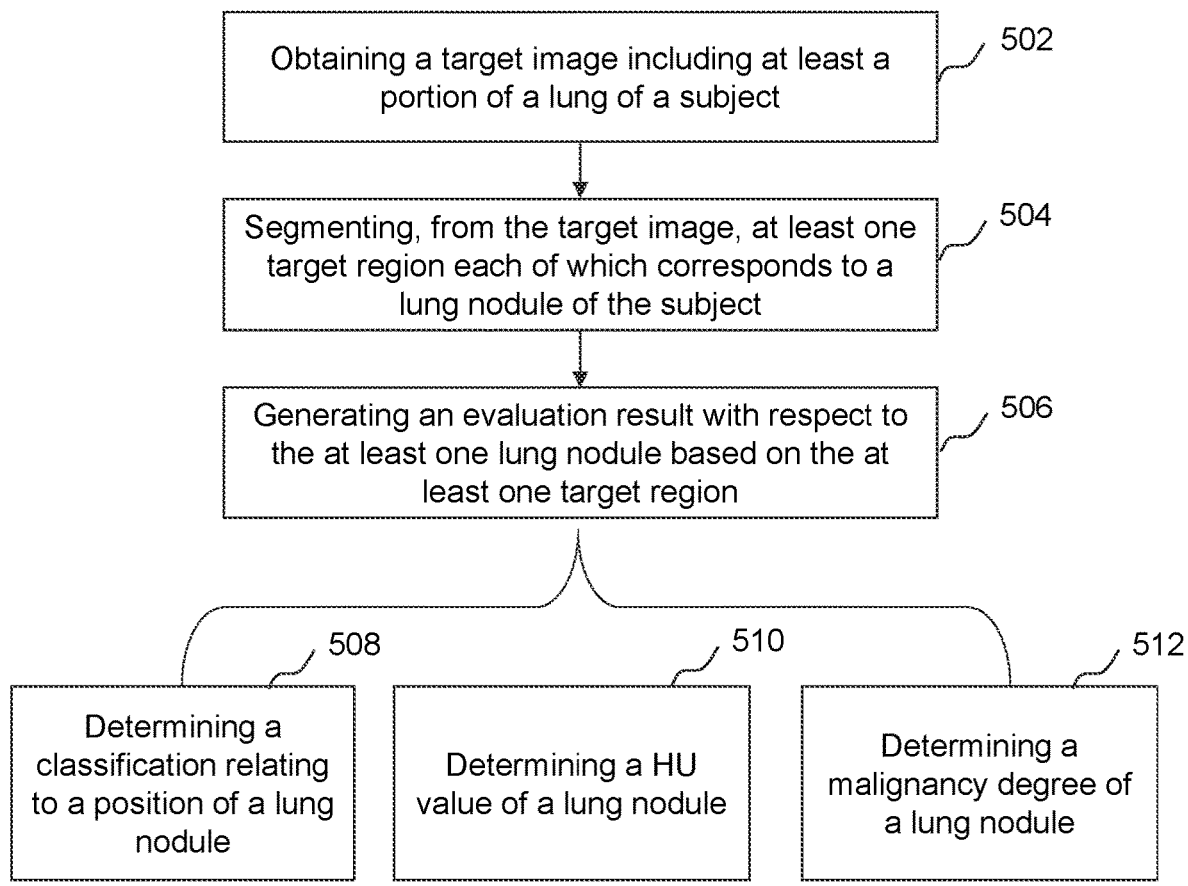
FIG. 5 is a flowchart illustrating an exemplary process for lung nodule evaluation according to some embodiments of the present disclosure.

FIG. 5 is a flowchart illustrating an exemplary process for lung nodule evaluation according to some embodiments of the present disclosure. In some embodiments, process 500 may be executed by the imaging system 100. For example, the process 500 may be implemented as a set of instructions (e.g., an application) stored in a storage device (e.g., the storage device 150, the storage 220, and/or the storage 390). In some embodiments, the processing device 140A (e.g., the processor 210 of the computing device 200, the CPU 340 of the mobile device 300, and/or one or more modules illustrated in FIG. 4A) may execute the set of instructions and may accordingly be directed to perform the process 500.

In 502, the processing device 140A (e.g., the acquisition module 402) may obtain a target image including at least a portion of a lung of a subject.

As used herein, the subject may include a biological subject and/or a non-biological subject that includes a lung (or a portion thereof). For example, the subject may be a human being, an animal, or a portion thereof. As another example, the subject may be a phantom that simulates a human lung. In some embodiments, the subject may be a patient (or a portion thereof), and the target image may include the left lung and the right lung of the patient. Each of the left lung and right lung may include multiple lung lobes. For example, the left lung may include 2 lung lobes, and the right lung may include 3 lung lobes.

In some embodiments, the target image may include a 2D image (e.g., a slice image), a 3D image, a 4D image (e.g., a series of 3D images over time), and/or any related image data (e.g., scan data, projection data), or the like. In some embodiments, the target image may include a medical image generated by a biomedical imaging technique as described elsewhere in this disclosure. For example, the target image may include a DR image, an MR image, a PET image, a CT image, a PET-CT image, a PET-MR image, an ultrasound image, etc. In some embodiments, the target image may include a single image or a set of images of the subject. For example, the target image may include multiple medical images of the subject obtained with different imaging parameters (different scan sequences, different imaging modalities, different postures of the target image, etc.).

In some embodiments, the target image may be generated based on image data acquired using the imaging device 110 of the imaging system 100 or an external imaging device. For example, the imaging device 110, such as a CT device, an MRI device, an X-ray device, a PET device, or the like, may be directed to scan the subject or a portion of the subject (e.g., the chest of the subject). The processing device 140A may generate the target image based on image data acquired by the imaging device 110. In some embodiments, the target image may be previously generated and stored in a storage device (e.g., the storage device 150, the storage 220, the storage 390, or an external source). The processing device 140A may retrieve the target image from the storage device.

In 504, the processing device 140A (e.g., the segmentation module 404) may segment, from the target image, at least one target region each of which corresponds to a lung nodule of the subject.

Figure 13:
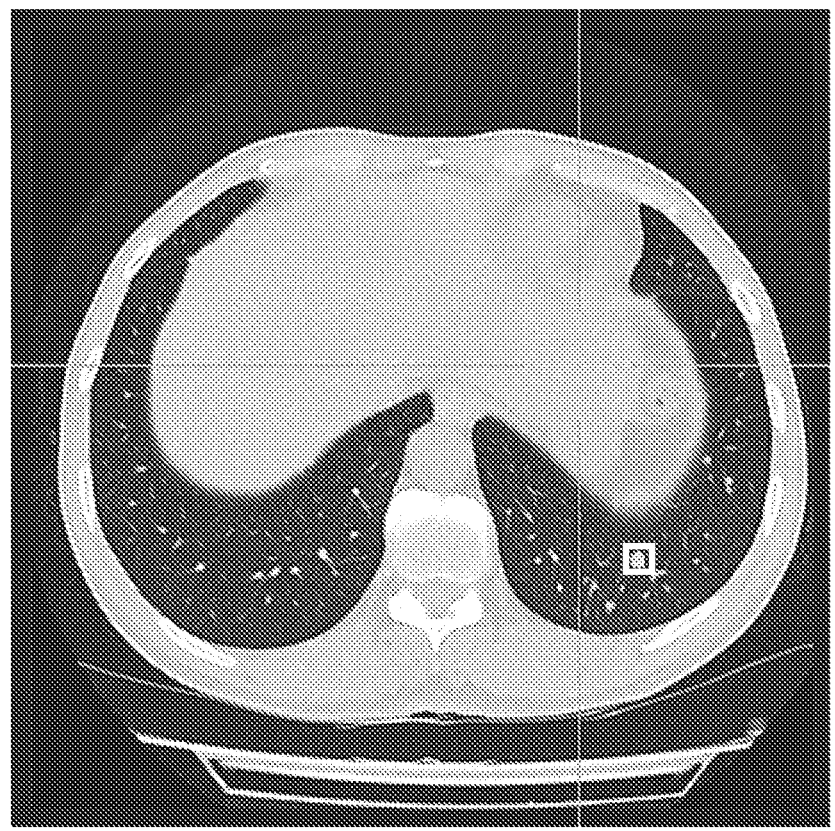
FIG. 13 is a schematic diagram illustrating an exemplary CT image of a lung nodule according to some embodiments of the present disclosure.

A target region corresponding to a lung nodule may be a region segmented from or identified in the target image that encloses the lung nodule. For example, the target region may include a bounding box enclosing the lung nodule. The bounding box may be 2-dimensional or 3-dimensional. For example, if the target image is a 2-dimensional image, the bounding box may have the shape of a square, a rectangle, a triangle, a polygon, a circle, an ellipse, an irregular shape, or the like. Merely by way of example, as shown in FIG. 13, a white square box is a bounding box enclosing a lung nodule. If the target image is a 3-dimensional image, the bounding box may have the shape of a cube or a cuboid. Optionally, the bounding box may be annotated in the target image. In some embodiments, during the segmentation of the target region, information relating to the bounding box of the target region may be determined. Exemplary information relating to the bounding box may include a shape, a size, a position (e.g., a coordinate of the center point of the bounding box), a probability that the bounding box includes a lung nodule, or the like, or any combination thereof. In some embodiments, the bounding box may be a cube, and the information relating to the bounding box may be represented as a multi-dimensional vector. Merely by way of example, the multi-dimensional vector may have seven dimensions N1-N7. The dimensions N1-N3 may represent an X-coordinate, a Y-coordinate, and a Z-coordinate of the center point of the bounding box in a world coordinate system, respectively. The dimensions N4-N6 may represent the length, the width, and the height of the bounding box, respectively. The dimension N7 may represent the probability that the bounding box includes a lung nodule.

In some embodiments, the target region corresponding to a lung nodule may be represented as a segmentation mask of the lung nodule generated based on the target image. For example, a portion corresponding to the lung nodule may be identified in the target image, and the segmentation mask may be generated based on the identified portion. In the segmentation mask, pixels (or voxels) corresponding to the lung nodule may be displayed in white, while pixels (or voxels) corresponding to other part of the subject may be displayed in black.

In some embodiments, the target region of a lung nodule may be segmented from the target image manually by a user (e.g., a doctor, an imaging specialist, a technician) by, for example, drawing a bounding box on the target image displayed on a user interface. Alternatively, the target image may be segmented by the processing device 140A automatically according to an image analysis algorithm (e.g., an image segmentation algorithm). For example, the processing device 140A may perform image segmentation on the target image using an image segmentation algorithm. Exemplary image segmentation algorithm may include a thresholding segmentation algorithm, a compression-based algorithm, an edge detection algorithm, a machine learning-based segmentation algorithm, or the like, or any combination thereof. Alternatively, the target region may be segmented by the processing device 140A semi-automatically based on an image analysis algorithm in combination with information provided by a user. Exemplary information provided by the user may include a parameter relating to the image analysis algorithm, a position parameter relating to a region to be segmented, an adjustment to, or rejection or confirmation of a preliminary segmentation result generated by the processing device 140A, etc.

In some embodiments, the processing device 140A may determine location information of the at least one lung nodule based on the target image, and then segment the at least one target region corresponding to the at least one lung nodule from the target image based on location information of the at least one lung nodule. For example, the position information of a lung nodule may include one or more positioning parameters of the lung nodule, and the target region corresponding to the lung nodule may be segmented from the target image according to the positioning parameter(s). In some embodiments, the positioning information of a lung nodule may be determined automatically by the processing device 140A and/or manually by a user through a terminal device.

In some embodiments, the at least one target region may be segmented from the target image using a lung nodule segmentation model. The lung nodule segmentation model may be a trained model (e.g., a machine learning model) used for lung nodule segmentation (or detection). Merely by way of example, the target image may be inputted into the lung nodule segmentation model, and the lung nodule segmentation model may output the at least one target region or information relating to the target region (e.g., position information of the bounding box(es) of the target region). In some embodiments, the lung nodule segmentation model may include a deep learning model, such as a Deep Neural Network (DNN) model, a Convolutional Neural Network (CNN) model, a Recurrent Neural Network (RNN) model, a Feature Pyramid Network (FPN) model, etc. Exemplary CNN models may include a V-Net model, a U-Net model, a Link-Net model, or the like, or any combination thereof.

In some embodiments, the processing device 140A may obtain the lung nodule segmentation model from one or more components of the imaging system 100 (e.g., the storage device 150, the terminals(s) 130) or an external source via a network (e.g., the network 120). For example, the lung nodule segmentation model may be previously trained by a computing device (e.g., the processing device 140B), and stored in a storage device (e.g., the storage device 150, the storage 220, and/or the storage 390) of the imaging system 100. The processing device 140A may access the storage device and retrieve the lung nodule segmentation model. In some embodiments, the lung nodule segmentation model may be generated according to a machine learning algorithm as described elsewhere in this disclosure (e.g., FIG. 4B and the relevant descriptions).

Merely by way of example, the lung nodule segmentation model may be trained according to a supervised learning algorithm by the processing device 140B or another computing device (e.g., a computing device of a vendor of the lung nodule segmentation model). The processing device 140B may obtain one or more first training samples and a first preliminary model. Each first training sample may include a first sample image of a sample subject and at least one sample target region of the first sample image, wherein the at least one sample target region of the first sample image may correspond to at least one lung nodule of the sample subject and be annotated (e.g., by a user) in the first sample image as a ground truth segmentation result. The first preliminary model to be trained may include one or more model parameters, such as the number (or count) of layers, the number (or count) of nodes, a first loss function, or the like, or any combination thereof. Before training, the first preliminary model may have one or more initial parameter values of the model parameter(s).

The training of the first preliminary model may include one or more first iterations to iteratively update the model parameters of the first preliminary model based on the first training sample(s) until a first termination condition is satisfied in a certain iteration. Exemplary first termination conditions may be that the value of a first loss function obtained in the certain iteration is less than a threshold value, that a certain count of iterations has been performed, that the first loss function converges such that the difference of the values of the loss function obtained in a previous iteration and the current iteration is within a threshold value, etc. The first loss function may be used to measure a discrepancy between a segmentation result predicted by the first preliminary model in an iteration and the ground truth segmentation result. For example, the first sample image of each first training sample may be inputted into the first preliminary model, and the first preliminary model may output at least one predicted target region of the first sample image of the training sample. The first loss function may be used to measure a difference between the predicted target region and the sample target region of each first training sample. Exemplary first loss functions may include a focal loss function, a log loss function, a cross-entropy loss, a Dice ratio, or the like. If the first termination condition is not satisfied in the current iteration, the processing device 140B may further update the first preliminary model to be used in a next iteration according to, for example, a backpropagation algorithm. If the first termination condition is satisfied in the current iteration, the processing device 140B may designate the first preliminary model in the current iteration as the lung nodule segmentation model.

In some embodiments, the processing device 140A may transmit the target image to another computing device (e.g., a computing device of a vendor of the lung nodule segmentation model). The computing device may segment the at least one target region from the target image and transmit the segmentation result back to the processing device 140A. In some embodiments, operation 504 may be omitted. The at least one target region may be previously segmented from the target image and stored in a storage device (e.g., the storage device 150, the storage 220, the storage 390, or an external source). The processing device 140A may retrieve the at least one target region from the storage device.

In 506, the processing device 140A (e.g., the generation module 406) may generate an evaluation result with respect to the at least one lung nodule based on the at least one target region.

In some embodiments, the evaluation result with respect to the at least one lung nodule may include an evaluation result of each of the at least one lung nodule (or a portion thereof). The evaluation result of a lung nodule may include one or more qualitative or quantitative parameters of the lung nodule. For example, the evaluation result of a lung nodule may include a position classification, a HU value, and/or a malignancy degree of the lung nodule. In some embodiments, the evaluation result of a lung nodule may be represented as an evaluation report of the lung nodule.

In some embodiments, operation 506 may be performed by performing one or more of operations 508, 510, and 512 as shown in FIG. 5. In some embodiments, one or more of operations 508, 510, and 512 may be performed for each of the at least one lung nodule (or a portion thereof). For illustration purposes, the implementation of operations 508, 510, and 512 for a lung nodule is described hereinafter as an example.

In 508, the processing device 140A (e.g., the generation module 406) may determine a classification relating to the position of the lung nodule. For example, based on the position of the lung nodule, the lung nodule may be classified as a pleural nodule, a non-pleural nodule, a perifissural nodule, a non-perifissural nodule, an intrapulmonary nodule, a lung nodule located at the left lung, a lung nodule located at the right lung, or the like, or any combination thereof.

For illustration purposes, the present disclosure is described with reference to the classification of the lung nodule into one or more of a pleural nodule, a non-pleural nodule, a perifissural nodule, a non-perifissural nodule, and an intrapulmonary nodule. A pleural nodule refers to a lung nodule located in a pleural space (e.g., a space between two pulmonary pleurae (known as visceral and parietal) of each lung of the subject). A non-pleural nodule refers to a lung nodule that is not located at the pleural space. For example, the non-pleural nodule may include a perifissural nodule or an intrapulmonary nodule. A perifissural nodule refers to a lung nodule located at or adjacent to a fissure of the subject. A non-perifissural nodule refers to a lung nodule that is not located at a fissure of the subject. For example, a non-perifissural nodule may include a pleural nodule and an intrapulmonary nodule. An intrapulmonary nodule refers to a lung nodule located at a lung lobe of the subject. The classification of a lung nodule described above is not intended to limit the scope of the present disclosure and the lung nodule may be classified in another suitable manner according to its position. More descriptions for the determination of a classification relating to the position of a lung nodule may be found elsewhere in the present disclosure (e.g., FIGS. 6-12 and the descriptions thereof).

Figure 16:
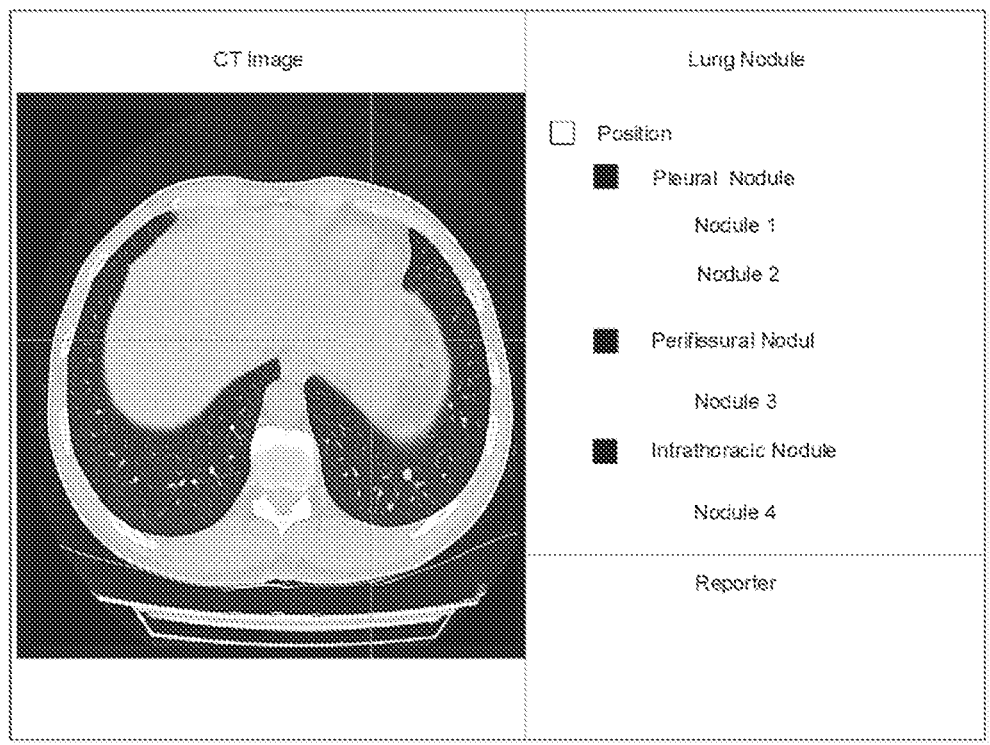
FIG. 16 illustrates an exemplary detection report of lung nodules according to some embodiments of the present disclosure.
Figure 17:
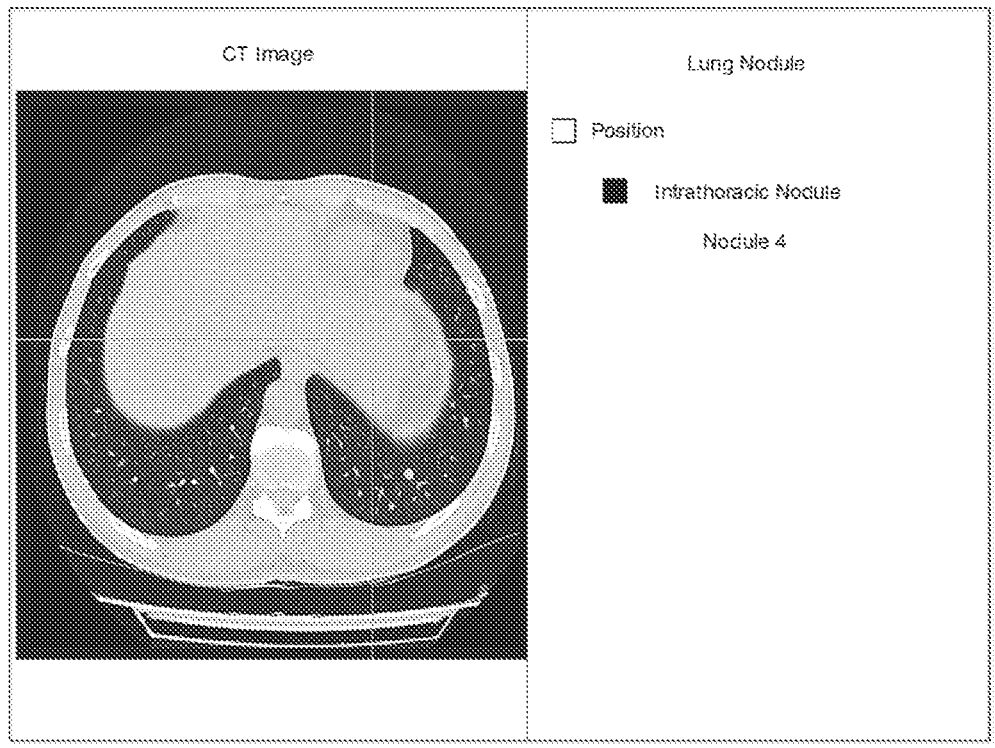
FIG. 17 illustrates an exemplary detection report of lung nodules according to some embodiments of the present disclosure.

In some embodiments, the processing device 140A may determine a classification relating to the position of each lung nodule of the subject, and generate a detection report, wherein the detection report may clearly and intuitively display the location and classification information of the at least one lung nodule of the subject. For example, FIG. 16 illustrates an exemplary detection report of the classification relating to the position of at least one lung nodule of a subject according to some embodiments of the present disclosure. As shown in FIG. 16, the subject includes two pleural nodules (nodule 1 and nodule 2), one perifissural nodule (nodule 3), and one intrapulmonary nodule (nodule 4). The detection report may clearly show the count of different types of the lung nodules. In addition, different types of lung nodules may be displayed or filtered according to different needs. As shown in FIG. 17, if the user only needs to view the intrapulmonary nodule of the subject, he or she may choose to filter out the pleural nodules (nodule 1 and nodule 2) and perifissural nodule (nodule 3), and only leave the intrapulmonary nodule (nodule 4). In such cases, the detection report only displays information relating to the intrapulmonary nodule, which is convenient for the user to view target information and improve the efficiency of information browsing.

In 510, the processing device 140A (e.g., the generation module 406) may determine a Hounsfield unit (HU) value of the lung nodule.

In some embodiments, the target image may be generated using an X-ray imaging device (e.g., a CT device, a DR device). A HU value of the lung nodule may be determined as a quantitative measurement for measuring X-ray attenuation during the scan of the subject. In some embodiments, the processing device 140A may determine one or more other coefficients, such as an attenuation coefficient, or the like, or any combination thereof, of the lung nodule. For illustration purposes, the determination of the HU value of the lung nodule is described as an example.

In some embodiments, the processing device 140A may identify one or more first transverse sections of the target region corresponding to the lung nodule. The processing device 140A may determine a target transverse section based on one or more first transverse sections. The processing device 140A may further determine a HU value of the lung nodule based on the target transverse section. More descriptions for the determination of a HU value of a lung nodule may be found elsewhere in the present disclosure (e.g., FIGS. 18-21 and the descriptions thereof).

In 512, the processing device 140A (e.g., the generation module 406) may determine a malignancy degree of the lung nodule.

As used herein, the malignancy degree of a lung nodule may reflect a probability that the lung nodule is malignant (e.g., a malignant cancer). In some embodiments, the malignant degree of the lung nodule may be represented in various forms. For example, the malignant degree may be represented as a score, and a greater score may indicate a higher probability that the lung nodule is malignant. As another example, the malignant degree may include a low-risk degree, a moderate-risk degree, and a high-risk degree. More descriptions for the determination of a malignancy degree of a lung nodule may be found elsewhere in the present disclosure (e.g., FIGS. 22-23 and the descriptions thereof).

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 500 may be accomplished with one or more additional operations not described and/or without one or more of the operations discussed above. For example, the process 500 may include an additional operation to transmit the evaluation result with respect to the at least one lung nodule to a terminal device (e.g., a terminal device 130 of a doctor) for display. As another example, operation 504 may be omitted, and the target image obtained in operation 502 may be annotated with one or more bounding boxes. Each of the bounding box(es) may enclose a lung nodule.

Figure 6:
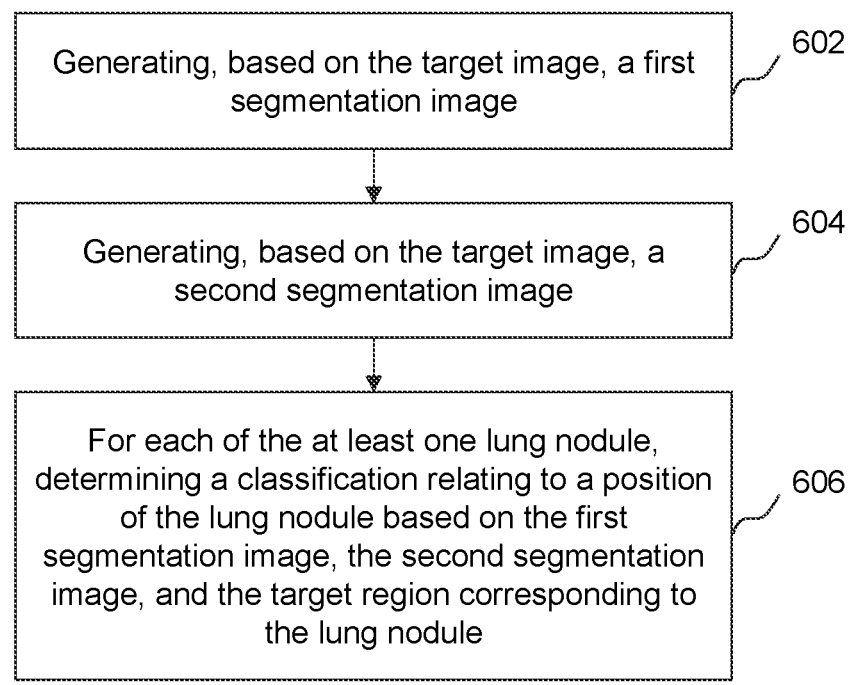
FIG. 6 is a flowchart illustrating an exemplary process for determining a classification relating to a position of a lung nodule according to some embodiments of the present disclosure.

FIG. 6 is a flowchart illustrating an exemplary process for determining a classification relating to a position of a lung nodule according to some embodiments of the present disclosure. In some embodiments, one or more operations of the process 600 may be performed to achieve at least part of operation 508 as described in connection with FIG. 5.

In 602, the processing device 140A (e.g., the generation module 406) may generate a first segmentation image based on the target image.

Figure 14:
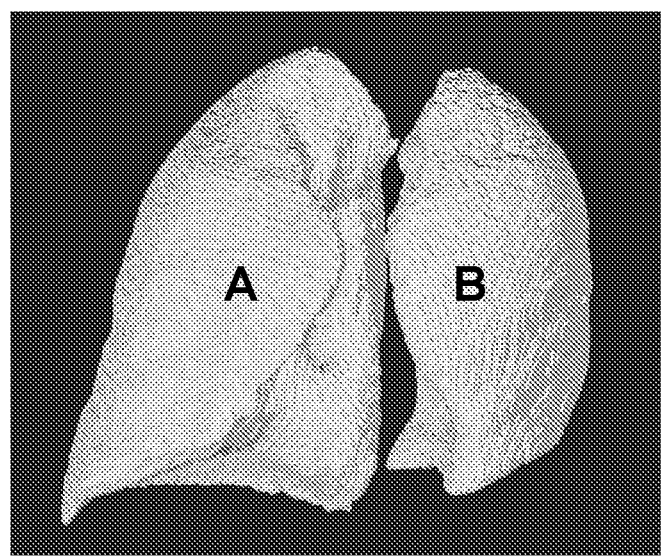
FIG. 14 illustrates an exemplary first segmentation image according to some embodiments of the present disclosure.

The first segmentation image may indicate the left lung and the right lung of the subject segmented from the target image. For example, FIG. 14 illustrates an exemplary first segmentation image according to some embodiments of the present disclosure. As shown in FIG. 14, a region A corresponds to the right lung of a patient, a region B corresponds to the left lung of the patient, and the remaining region (i.e., the black region) is a background region. Using the first segmentation image, the regions corresponding to the left and right lungs may be distinguished from the background region. The generation of the first segmentation image may facilitate a subsequent classification of a pleural nodule and a non-pleural nodule.

In some embodiments, the left and right lungs may be segmented from the target image manually by a user, automatically by the processing device 140A, or semi-automatically. For example, the segmentation of the left and right lungs may be performed in a similar manner as that of the at least one lung nodule as described in connection with operation 504, and the descriptions thereof are not repeated here. In some embodiments, the left and right lungs may be segmented from the target image according to a second segmentation image relating to the at least one lung lobe of the subject. More descriptions regarding the second segmentation image may be found elsewhere in the present disclosure. See, e.g., operation 604 and relevant descriptions thereof.

In some embodiments, the processing device 140A may generate the first segmentation image by processing the target image using a lung segmentation model. The lung segmentation model may be a trained model (e.g., a machine learning model) used for lung segmentation. For example, the target image may be inputted into the lung segmentation model, and the lung segmentation model may output the first segmentation image and/or information (e.g., position information and/or contour information) relating to the left and right lungs of the subject.

Merely by way of example, the lung segmentation model may be trained according to a supervised learning algorithm by the processing device 140B or another computing device (e.g., a computing device of a vendor of the lung segmentation model). For example, the processing device 140B may obtain one or more second training samples and a second preliminary model. Each second training sample may include a second sample image of a sample subject and a sample first segmentation image of the sample subject, wherein the right lung and the left lung of the sample subject may be annotated (e.g., by a user) in the sample first segmentation image as a ground truth segmentation result. In some embodiments, the sample first segmentation image of a second training sample may be represented as a segmentation mask of the left and right lungs of the sample subject of the second training sample. The second preliminary model to be trained may include one or more model parameters, such as the number (or count) of layers, the number (or count) of nodes, a second loss function, or the like, or any combination thereof. Before training, the second preliminary model may have one or more initial parameter values of the model parameter(s).

The training of the second preliminary model may include one or more second iterations to iteratively update the model parameters of the second preliminary model based on the second training sample(s) until a second termination condition is satisfied in a certain iteration. Exemplary second termination conditions may be that the value of a second loss function obtained in the certain iteration is less than a threshold value, that a certain count of iterations has been performed, that the second loss function converges such that the difference of the values of the loss function obtained in a previous iteration and the current iteration is within a threshold value, etc. The second loss function may be used to measure a discrepancy between a segmentation result predicted by the second preliminary model in an iteration and the ground truth segmentation result. For example, the second sample image of each second training sample may be inputted into the second preliminary model, and the second preliminary model may output a predicted first segmentation image of the left and right lungs of the sample subject of the training sample. The second loss function may be used to measure a difference between the predicted first segmentation image and the sample first segmentation image of each second training sample. Exemplary second loss functions may include a focal loss function, a log loss function, a cross-entropy loss, a Dice ratio, or the like. If the second termination condition is not satisfied in the current iteration, the processing device 140B may further update the second preliminary model to be used in a next iteration according to, for example, a backpropagation algorithm. If the second termination condition is satisfied in the current iteration, the processing device 140B may designate the second preliminary model in the current iteration as the lung segmentation model.

In 604, the processing device 140A (e.g., the generation module 406) may generate a second segmentation image based on the target image.

Figure 15:
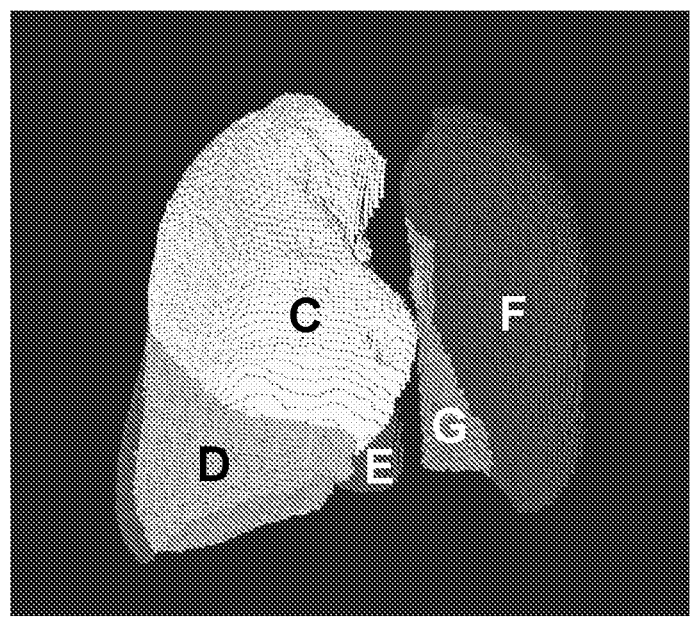
FIG. 15 illustrates an exemplary second segmentation image according to some embodiments of the present disclosure.

In some embodiments, the second segmentation image may indicate at least one lung lobe of the subject segmented from the target image. For example, FIG. 15 illustrates an exemplary second segmentation image according to some embodiments of the present disclosure. As shown in FIG. 15, a region C corresponds to the upper lobe of the right lung, a region D corresponds to the middle lobe of the right lung, a region E corresponds to the lower lobe of the right lung, a region F corresponds to the upper lobe of the left lung, a region G corresponds the lower lobe of the left lung, and the remaining region (i.e., the black region) is a background region. Using the second segmentation image, the regions corresponding to the lung lobes of the left and right lungs may be distinguished from the background region. The generation of the second segmentation image may facilitate a subsequent classification of a perifissural nodule and a non-perifissural nodule.

In some embodiments, the lung lobes of the left and right lungs may be segmented from the target image manually by a user, automatically by the processing device 140A, or semi-automatically. For example, the segmentation of the lung lobes of the left and right lungs may be performed in a similar manner as that of the at least one lung nodule as described in connection with operation 504, and the descriptions thereof are not repeated here.

In some embodiments, the processing device 140A may generate the second segmentation image by processing the target image using a lung lobe segmentation model. The lung lobe segmentation model may be a trained model (e.g., a machine learning model) used for lung lobe segmentation. For example, the target image may be inputted into the lung lobe segmentation model, and the lung lobe segmentation model may output the second segmentation image and/or information (e.g., position information and/or contour information) relating to the lung lobes of the subject.

Merely by way of example, the lung lobe segmentation model may be trained according to a supervised learning algorithm by the processing device 140B or another computing device (e.g., a computing device of a vendor of the lung lobe segmentation model). For example, the processing device 140B may obtain one or more third training samples and a third preliminary model (e.g., a V-net model). Each third training sample may include a third sample image of a sample subject and a sample second segmentation image of the sample subject, wherein the lung lobes of the right lung and the left lung of the sample subject may be annotated (e.g., by a user) in the sample second segmentation image as a ground truth segmentation result. For example, the sample second segmentation image of a third training sample may be represented as a segmentation mark of the lung lobes of the sample subject of the third training sample. In some embodiments, a third training sample may further include a sample first segmentation image of the sample subject, wherein the left and right lungs of the sample subject may be annotated in the sample first segmentation image. For example, the sample first segmentation image may be represented as a segmentation mark of the left and right lungs of the sample subject. The third preliminary model to be trained may include one or more model parameters, such as the number (or count) of layers, the number (or count) of nodes, a third loss function, or the like, or any combination thereof. Before training, the third preliminary model may have one or more initial parameter values of the model parameter(s).

The training of the third preliminary model may include one or more third iterations to iteratively update the model parameters of the third preliminary model based on the third training sample(s) until a third termination condition is satisfied in a certain iteration. Exemplary third termination conditions may be that the value of a third loss function obtained in the certain iteration is less than a threshold value, that a certain count of iterations has been performed, that the third loss function converges such that the difference of the values of the loss function obtained in a previous iteration and the current iteration is within a threshold value, etc. The third loss function may be used to measure a discrepancy between a segmentation result predicted by the third preliminary model in an iteration and the ground truth segmentation result. For example, the third sample image of each third training sample may be inputted into the third preliminary model, and the third preliminary model may output a predicted second segmentation image of the lung lobes of the sample subject of the training sample. The third loss function may be used to measure a difference between the predicted second segmentation image and the sample second segmentation image of each third training sample. Exemplary third loss functions may include a focal loss function, a log loss function, a cross-entropy loss, a Dice ratio, or the like. If the third termination condition is not satisfied in the current iteration, the processing device 140B may further update the third preliminary model to be used in a next iteration according to, for example, a backpropagation algorithm. If the third termination condition is satisfied in the current iteration, the processing device 140B may designate the third preliminary model in the current iteration as the lung lobe segmentation model.

In 606, for each of the at least one lung nodule, the processing device 140A (e.g., the generation module 406) may determine a classification relating to the position of the lung nodule based on the first segmentation image, the second segmentation image, and the target region corresponding to the lung nodule.

In some embodiments, the processing device 140A may determine the position information of a lung nodule. The position information of the lung nodule may indicate, for example, whether the lung nodule is located at or near the pleura space, whether the lung nodule is located at or near a fissure, and/or whether the lung nodule is located at or near a lung lobe, etc. For example, if the lung nodule is located within a certain threshold distance with respect to a reference subject (e.g., a fissure), the lung nodule may be regarded as being located near the reference subject. The processing device 140A may further determine a classification relating to the position of the lung nodule based on the position information of the lung nodule. More descriptions for determination of a classification relating to a position of the lung nodule may be found elsewhere in the present disclosure (e.g., FIGS. 7-12 and the descriptions thereof).

Figure 7:
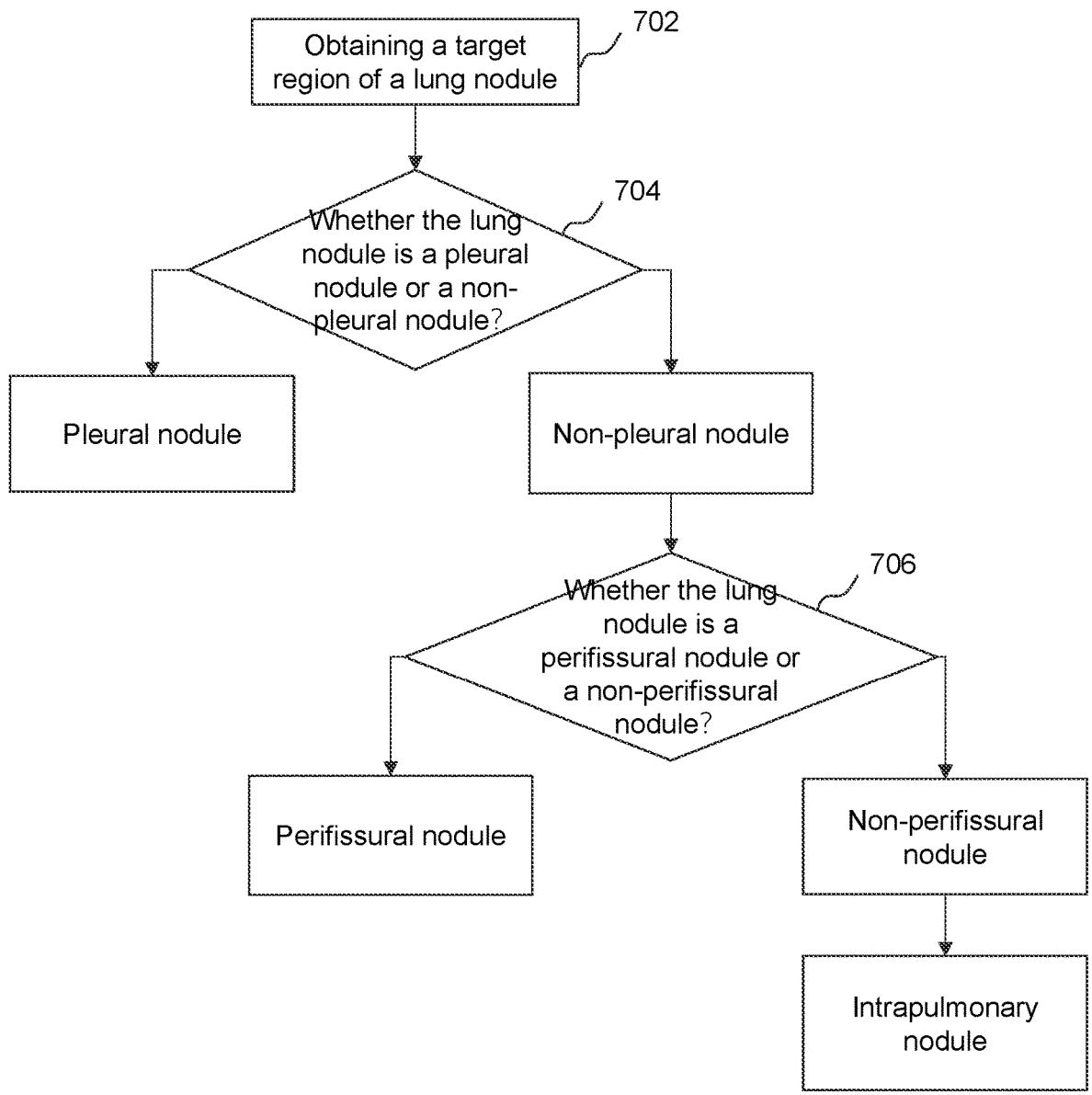
FIG. 7 is a flowchart illustrating an exemplary process for determining a classification relating to a position of a lung nodule according to some embodiments of the present disclosure.

FIG. 7 is a flowchart illustrating an exemplary process for determining a classification relating to a position of a lung nodule according to some embodiments of the present disclosure. In some embodiments, one or more operations of the process 700 may be performed to achieve at least part of operation 606 as described in connection with FIG. 6.

In 702, the processing device 140A (e.g., the acquisition module 402) may obtain a target region of a lung nodule.

In some embodiments, the target region may be obtained by performing operation 504 as described in connection with FIG. 5.

In 704, the processing device 140A (e.g., the generation module 406) may determine whether the lung nodule is a pleural nodule or a non-pleural nodule based on the first segmentation image and the target region corresponding to the lung nodule.

In some embodiments, the processing device 140A may perform a two-stage determination in operation 704. For example, the processing device 140A may first generate a first preliminary (or rough) determination result of whether the lung nodule is a candidate pleural nodule or a non-pleural nodule. If the lung nodule is a candidate pleural nodule, the processing device 140A may further generate a first final determination result by verifying whether the candidate pleural nodule is a pleural nodule or a non-pleural nodule. Merely by way of example, the first preliminary determination result may be generated based on a bounding box of the target region corresponding to the lung nodule, and the first final determination result may be generated based on a pleural nodule identification model. In some embodiments, the processing device 140A may directly determine whether the lung nodule is a pleural nodule or a non-pleural nodule. For example, the processing device 140A may directly generate the first final determination result without generating the preliminary determination result. In some embodiments, the processing device 140A may determine whether the lung nodule is a pleural nodule or a non-pleural nodule by performing one or more operations of process 800 as described in connection with FIG. 8.

In response to determining that the lung nodule is a non-pleural nodule, the processing device 140A may proceed to operation 706.

In 706, the processing device 140A (e.g., the generation module 406) may determine whether the lung nodule is a perifissural nodule or a non-perifissural nodule based on the second segmentation image and the target region corresponding to the lung nodule.

In some embodiments, the processing device 140A may perform a two-stage determination in operation 706. For example, the processing device 140A may first generate a second preliminary (or rough) determination result of whether the lung nodule is a candidate perifissural nodule or a non-perifissural nodule. If the lung nodule is a candidate perifissural nodule, the processing device 140A may further generate a second final determination result by verifying whether the candidate perifissural nodule is a perifissural nodule or a non-perifissural nodule. Merely by way of example, the second preliminary determination result may be generated based on a bounding box of the target region corresponding to the lung nodule, and the second final determination result may be generated based on a perifissural nodule identification model. In some embodiments, the processing device 140A may directly determine whether the lung nodule is a perifissural nodule or a non-perifissural nodule. For example, the processing device 140A may directly generate the second final determination result without generating the preliminary determination result. In some embodiments, the processing device 140A may determine whether the lung nodule is a perifissural nodule or a non-perifissural nodule by performing one or more operations of process 1000 as described in connection with FIG. 10.

In response to determining that the lung nodule is a non-perifissural nodule, the processing device 140A may determine that the lung nodule is an intrapulmonary nodule.

Figure 8:
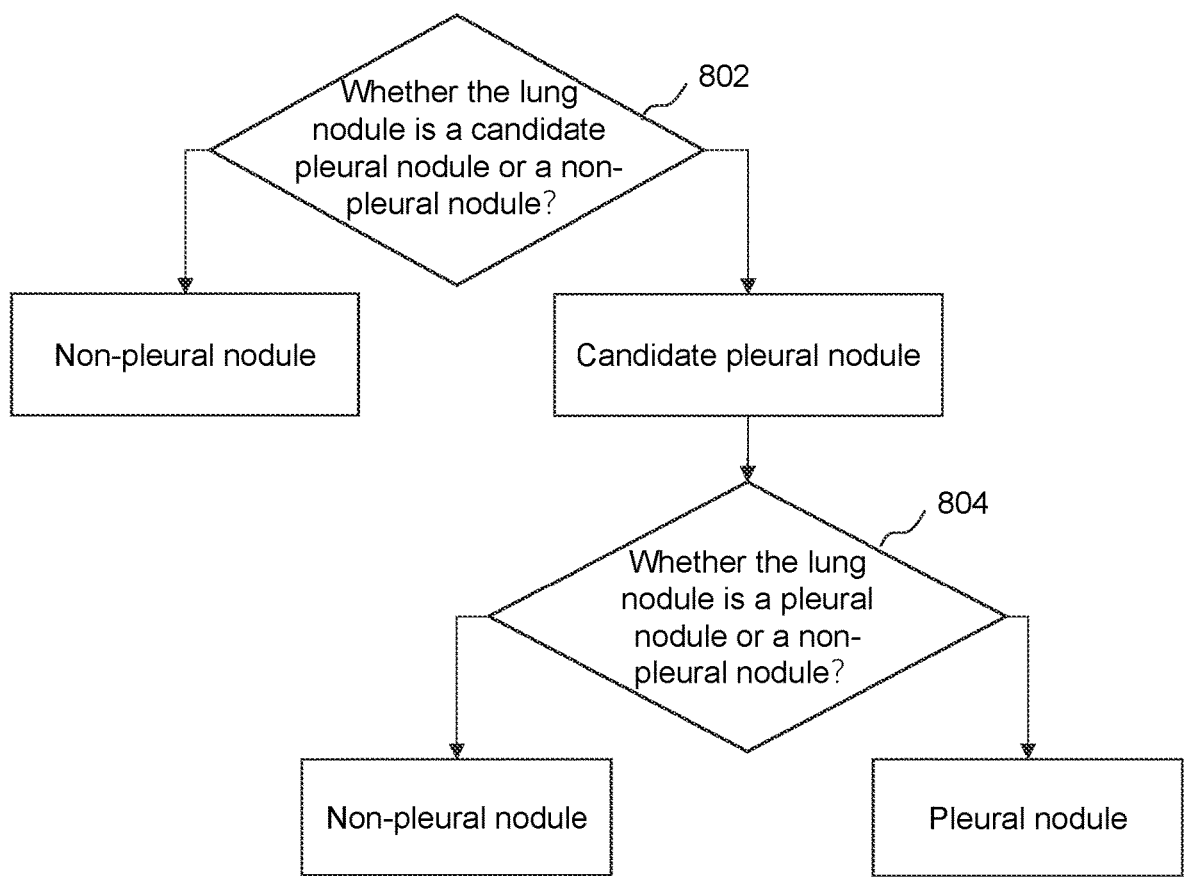
FIG. 8 is a flowchart illustrating an exemplary process for determining whether a lung nodule is a pleural nodule or a non-pleural nodule according to some embodiments of the present disclosure.

FIG. 8 is a flowchart illustrating an exemplary process for determining whether a lung nodule is a pleural nodule or a non-pleural nodule according to some embodiments of the present disclosure. In some embodiments, one or more operations of the process 800 may be performed to achieve at least part of operation 704 as described in connection with FIG. 7.

In 802, the processing device 140A (e.g., the generation module 406) may determine whether the lung nodule is a candidate pleural nodule or a non-pleural nodule based on the first segmentation image and the target region corresponding to the lung nodule. For example, the processing device 140A may determine whether the lung nodule is a candidate pleural nodule or a non-pleural nodule by performing one or more operations of process 900 as described in connection with FIG. 9.

In response to determining that the lung nodule is a candidate pleural nodule, the processing device 140A may proceed to operation 804, in which the processing device 140A (e.g., the generation module 406) may verify whether the lung nodule is a pleural nodule or a non-pleural nodule. For example, the processing device 140A may verify whether the lung nodule is a pleural nodule or a non-pleural nodule based on the first segmentation image and the target region using a pleural nodule identification model. The pleural nodule identification model may be a trained model (e.g., a machine learning model) used for pleural nodule identification. For example, the first segmentation image and the target region corresponding to the candidate pleural nodule may be inputted into the pleural nodule identification model, and the pleural nodule identification model may output a determination result of whether the lung nodule is a pleural nodule or a non-pleural nodule. In some embodiments, the pleural nodule identification model may be a two-channel model that may receive and process two inputs (e.g., the target region and the first segmentation image).

In some embodiments, the pleural nodule identification model may be trained according to a supervised learning algorithm by the processing device 140B or another computing device (e.g., a computing device of a vendor of the pleural nodule identification model). For example, the processing device 140B may obtain one or more fourth training samples and a fourth preliminary model. Each fourth training sample may include a sample first segmentation image of a sample subject, a sample image of a sample lung nodule of the sample subject, and a classification of the sample lung nodule (e.g., whether the sample lung nodule is a pleural nodule or a non-pleural nodule). The classification of the sample lung nodule of each fourth training sample may be used as a ground truth identification result. The fourth preliminary model to be trained may include one or more model parameters, such as the number (or count) of layers, the number (or count) of nodes, a fourth loss function, or the like, or any combination thereof. Before training, the fourth preliminary model may have one or more initial parameter values of the model parameter(s).

The training of the fourth preliminary model may include one or more fourth iterations to iteratively update the model parameters of the fourth preliminary model based on the fourth training sample(s) until a fourth termination condition is satisfied in a certain iteration. Exemplary fourth termination conditions may be that the value of a fourth loss function obtained in the certain iteration is less than a threshold value, that a certain count of iterations has been performed, that the fourth loss function converges such that the difference of the values of the loss function obtained in a previous iteration and the current iteration is within a threshold value, etc. The fourth loss function may be used to measure a discrepancy between a predicted identification result generated by the fourth preliminary model in an iteration and the ground truth identification result. For example, for each fourth training sample, the sample first segmentation image and the sample image of the fourth training sample may be inputted into the fourth preliminary model, and the fourth preliminary model may output a predicted identification result of whether the sample lung nodule of the fourth training sample is a pleural nodule or a non-pleural nodule. The fourth loss function may be used to measure a difference between the predicted identification result and the ground truth identification result of each fourth training sample. Exemplary fourth loss functions may include a focal loss function, a log loss function, a cross-entropy loss, a Dice ratio, or the like. If the fourth termination condition is not satisfied in the current iteration, the processing device 140B may further update the fourth preliminary model to be used in a next iteration according to, for example, a backpropagation algorithm. If the fourth termination condition is satisfied in the current iteration, the processing device 140B may designate the fourth preliminary model in the current iteration as the pleural nodule identification model.

In the process 800, the processing device 140A may first generate a preliminary determination result of whether the lung nodule is a candidate pleural nodule or a non-pleural nodule, and further verify whether the lung nodule is a pleural nodule or non-pleural nodule if the lung nodule is a candidate pleural nodule. Based on the preliminary determination result, a lung nodule that is far away from the pleural cavity of the subject may be filtered out and a lung nodule near the pleural cavity may be retained. By performing a two-stage determination, the accuracy of the determination result of whether the lung nodule is a pleural nodule may be improved.

Figure 9:
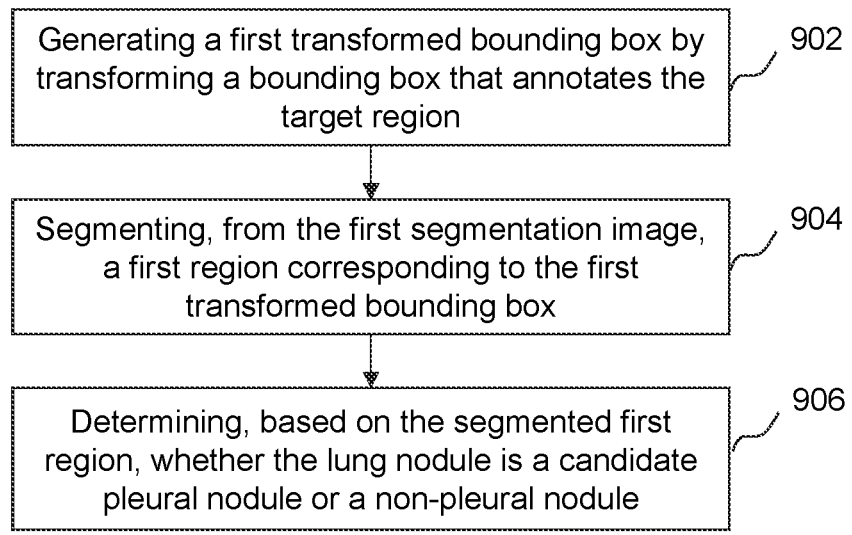
FIG. 9 is a flowchart illustrating an exemplary process for determining whether a lung nodule is a candidate pleural nodule or a non-pleural nodule according to some embodiments of the present disclosure.

FIG. 9 is a flowchart illustrating an exemplary process for determining whether a lung nodule is a candidate pleural nodule or a non-pleural nodule according to some embodiments of the present disclosure. In some embodiments, one or more operations of the process 900 may be performed to achieve at least part of operation 802 as described in connection with FIG. 8.

As described in connection with operation 504, the target region corresponding to the lung nodule may be annotated by a bounding box. The processing device 140A may determine whether the lung nodule is a candidate pleural nodule or a non-pleural nodule based on the bounding box.

In 902, the processing device 140A (e.g., the generation module 406) may generate a first transformed bounding box by transforming the bounding box that annotates the target region.

For example, in the transformation of the bounding box, the position of a center point of the bounding box may remain unchanged, and the bounding box may be enlarged according to a preset enlarging ratio. The preset enlarging ratio may be determined according to a default setting of the imaging system 100, or manually set by a user, or determined by the processing device 140A according to an actual need. For example, the preset enlarging ratio may be determined based on a plurality of sample images of a plurality of sample pleural nodules. Merely by way of example, the preset enlarging ratio may be determined based on a position of a sample pleural nodule relative to the boundary of a lung in each sample image. In some embodiments, the enlarged bounding box (i.e., the first transformed bounding box) may include the target region and also a portion of the background region of the target image.

In 904, the processing device 140A (e.g., the generation module 406) may segment, from the first segmentation image, a first region corresponding to the first transformed bounding box.

In some embodiments, the processing device 140A may determine or obtain feature information of the first transformed bounding box. The feature information of the first transformed bounding box may include a shape, a size, a position (e.g., a coordinate of the center point in a coordinate system, such as a world coordinate system), or the like, or any combination thereof, of the first transformed bounding box. The processing device 140A may segment the first region corresponding to the first transformed bounding box from the first segmentation image based on the feature information of the first transformed bounding box. For example, the size of the first region may be equal to the first transformed bounding box. Additionally or alternatively, the position of the center point of the first region (e.g., represented as a coordinate in the world coordinate system) may be the same as that of the first transformed bounding box.

In 906, the processing device 140A (e.g., the generation module 406) may determine, based on the segmented first region, whether the lung nodule is a candidate pleural nodule or a non-pleural nodule.

In some embodiments, the first region may include one or more target image elements (e.g., pixels or voxels) corresponding to the left and right lungs of the subject and/or one or more background image elements corresponding to the background region of the first segmentation image. For example, the processing device 140A may determine a first ratio of the count of the background image elements to the total count of the image elements of the first region. The processing device 140A may further determine whether the lung nodule is a candidate pleural nodule or a non-pleural nodule based on the first ratio. Merely by way of example, if the first ratio exceeds a first threshold ratio, the processing device 140A may determine that the lung nodule is a candidate pleural nodule; if the first ratio does not exceed the first threshold ratio, the processing device 140A may determine that the lung nodule is a non-pleural nodule.

As another example, the processing device 140A may determine a second ratio of the count of the target image elements the total count of the image elements in the segmented first region. The processing device 140A may further determine whether the lung nodule is a candidate pleural nodule or a non-pleural nodule based on the second ratio. Merely by way of example, if the second ratio is less than a second threshold ratio, the processing device 140A may determine that the lung nodule is a candidate pleural nodule; if the second ratio is not less than the second threshold ratio, the processing device 140A may determine that the lung nodule is a non-pleural nodule.

As yet another example, the processing device 140A may determine a third ratio of the count of the background image elements to the count of the target image elements. The processing device 140A may further determine whether the lung nodule is a candidate pleural nodule or a non-pleural nodule based on the third ratio. Merely by way of example, if the third ratio is greater than a third threshold ratio, the processing device 140A may determine that the lung nodule is a candidate pleural nodule; if the third ratio is not greater than the third threshold ratio, the processing device 140A may determine that the lung nodule is a non-pleural nodule.

In some embodiments, the first threshold ratio, the second threshold ratio, and/or the third threshold ratio may be set by a user, or according to a default setting of the imaging system 100, or determined by the processing device 140A according to an actual need. For example, for each sample image of a sample pleural nodule, a sample first region may be determined in a similar manner as how the first region corresponding to the target region is determined. One or more of the first threshold ratio, the second threshold ratio, and the third threshold ratio may be determined based on the sample first regions. Merely by way of example, for each sample first region, the processing device 140A may determine a ratio of the count of target image elements to the count of background image elements in the sample first region. The processing device 140A may further determine the third threshold ratio based on the ratio corresponding to each sample first region.

In some embodiments, the 800 and/or the process 900 may include one or more additional operations. Additionally or alternatively, one or more operations of the process 800 and/or the process 900 described above may be omitted. For example, operation 802 may be omitted, and the processing device 140A may merely perform operation 804. As another example, operation 804 may be omitted. In 802, the processing device 140A may determine whether the lung nodule is a pleural nodule or a non-pleural nodule based on one or more of the first ratio, the second ratio, and the third ratio as aforementioned.

Figure 10:
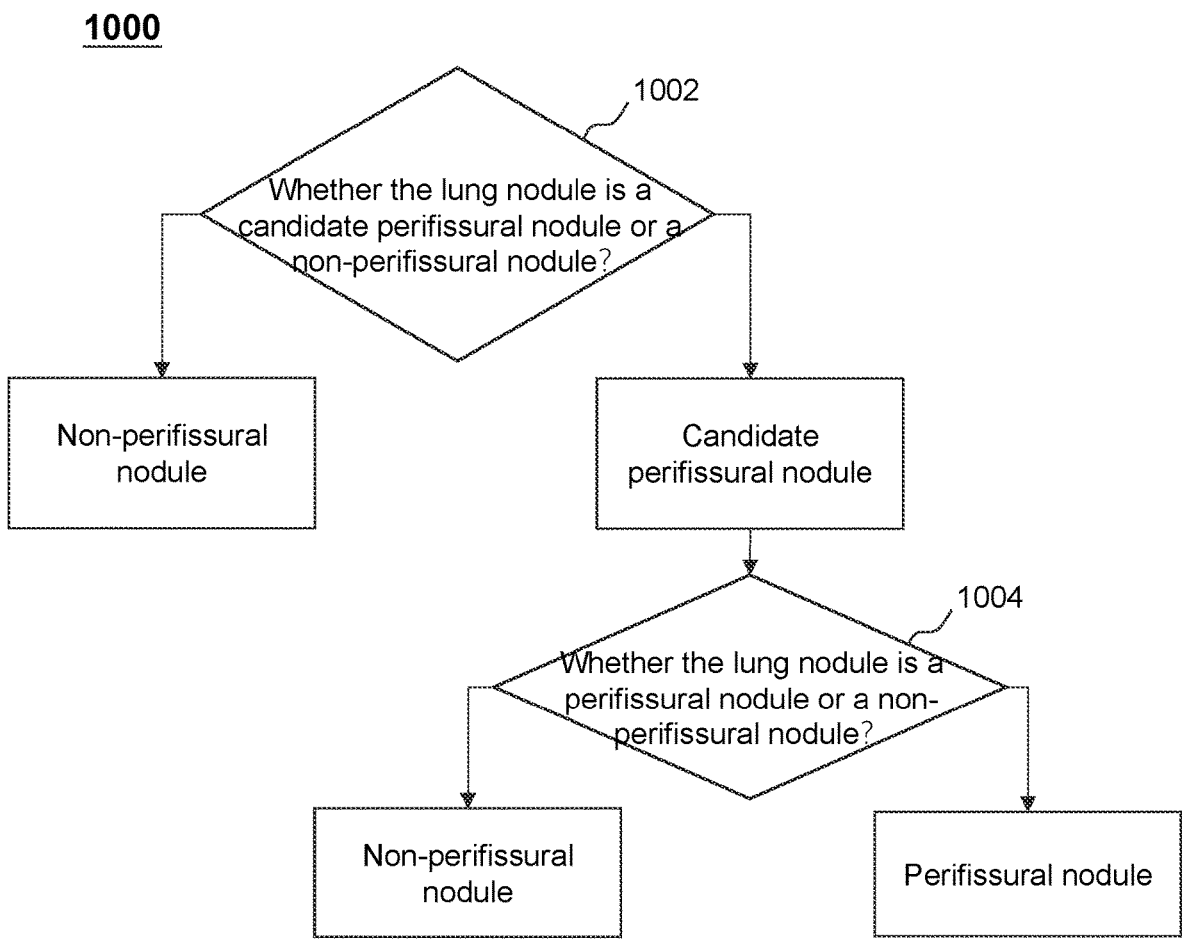
FIG. 10 is a flowchart illustrating an exemplary process for determining whether a lung nodule is a perifissural nodule or a non-perifissural nodule according to some embodiments of the present disclosure.

FIG. 10 is a flowchart illustrating an exemplary process for determining whether a lung nodule is a perifissural nodule or a non-perifissural nodule according to some embodiments of the present disclosure. In some embodiments, one or more operations of the process 1000 may be performed to achieve at least part of operation 706 as described in connection with FIG. 7.

In 1002, the processing device 140A (e.g., the generation module 406) may determine whether the lung nodule is a candidate perifissural nodule or a non-perifissural nodule based on the second segmentation image and the target region corresponding to the lung nodule. For example, the processing device 140A may determine whether the lung nodule is a candidate perifissural nodule or a non-perifissural nodule by performing one or more operations of process 1100 as described in connection with FIG. 11.

In response to determining that the lung nodule is a candidate perifissural nodule, the processing device 140A may proceed to operation 1004, in which the processing device 140A (e.g., the generation module 406) may verify whether the lung nodule is a perifissural nodule or a non-perifissural nodule. For example, the processing device 140A may verify whether the lung nodule is a perifissural nodule or a non-perifissural nodule based on the second segmentation image and the target region using a perifissural nodule identification model. The perifissural nodule identification model may be a trained model (e.g., a machine learning model) used for perifissural nodule identification. Merely by way of example, the second segmentation image and the target region of the candidate perifissural nodule may be inputted into the perifissural nodule identification model, and the perifissural nodule identification model may output a determination result of whether the lung nodule is a perifissural nodule or a non-perifissural nodule. In some embodiments, the perifissural nodule identification model may be a two-channel model that may receive and process two inputs (e.g., the target region and the second segmentation image).

In some embodiments, the perifissural nodule identification model may be trained according to a supervised learning algorithm by the processing device 140B or another computing device (e.g., a computing device of a vendor of the perifissural nodule identification model). For example, the processing device 140B may obtain one or more fifth training samples and a fifth preliminary model. Each fifth training sample may include a sample second segmentation image of a sample subject, a sample image of a sample lung nodule of the sample subject, and a classification of the sample lung nodule (e.g., whether the sample lung nodule is a perifissural nodule or a non-perifissural nodule). The classification of the sample lung nodule of each fifth training sample may be used as a ground truth identification result. The fifth preliminary model to be trained may include one or more model parameters, such as the number (or count) of layers, the number (or count) of nodes, a fifth loss function, or the like, or any combination thereof. Before training, the fifth preliminary model may have one or more initial parameter values of the model parameter(s).

The training of the fifth preliminary model may include one or more fifth iterations to iteratively update the model parameters of the fifth preliminary model based on the fifth training sample(s) until a fifth termination condition is satisfied in a certain iteration. Exemplary fifth termination conditions may be that the value of a fifth loss function obtained in the certain iteration is less than a threshold value, that a certain count of iterations has been performed, that the fifth loss function converges such that the difference of the values of the loss function obtained in a previous iteration and the current iteration is within a threshold value, etc. The fifth loss function may be used to measure a discrepancy between a predicted identification result generated by the fifth preliminary model in an iteration and the ground truth identification result. For example, for each fifth training sample, the sample second segmentation image and the sample image of the fifth training sample may be inputted into the fifth preliminary model, and the fifth preliminary model may output a predicted identification result of whether the sample lung nodule of the fifth training sample is a perifissural nodule or non-perifissural nodule. The fifth loss function may be used to measure a difference between the predicted identification result and the ground truth identification result of each fifth training sample. Exemplary fifth loss functions may include a focal loss function, a log loss function, a cross-entropy loss, a Dice ratio, or the like. If the fifth termination condition is not satisfied in the current iteration, the processing device 140B may further update the fifth preliminary model to be used in a next iteration according to, for example, a backpropagation algorithm. If the fifth termination condition is satisfied in the current iteration, the processing device 140B may designate the fifth preliminary model in the current iteration as the perifissural nodule identification model.

In the process 1000, the processing device 140A may first generate a preliminary determination result of whether the lung nodule is a candidate perifissural nodule or a non-perifissural nodule, and further verify whether the lung nodule is a perifissural nodule or non-perifissural nodule if the lung nodule is a candidate perifissural nodule. Based on the preliminary determination result, a lung nodule that is far away from a fissure of the subject may be filtered out and a lung nodule near a fissure of the subject may be retained. By performing a two-stage determination, the accuracy of the determination result of whether the lung nodule is a perifissural nodule may be improved.

Figure 11:
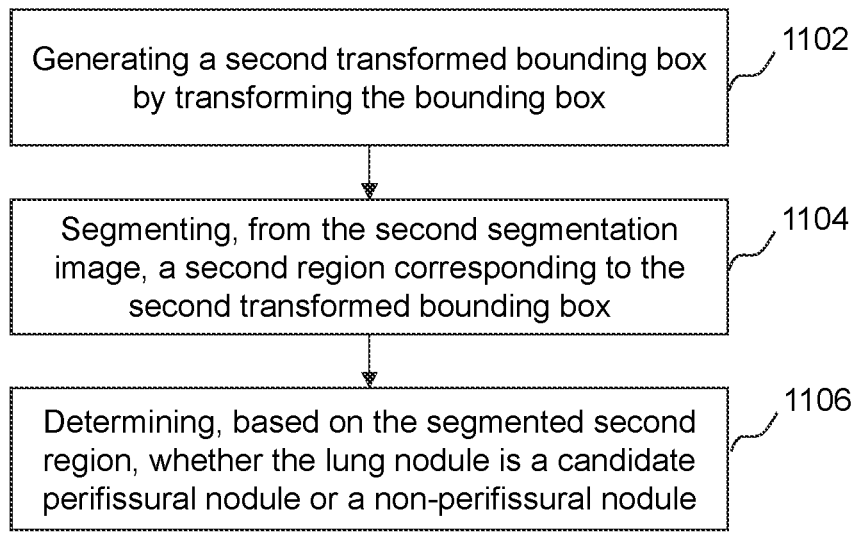
FIG. 11 is a flowchart illustrating an exemplary process for determining whether a lung nodule is a candidate perifissural nodule or a non-perifissural nodule according to some embodiments of the present disclosure.

FIG. 11 is a flowchart illustrating an exemplary process for determining whether a lung nodule is a candidate perifissural nodule or a non-perifissural nodule according to some embodiments of the present disclosure. In some embodiments, one or more operations of the process 1100 may be performed to achieve at least part of operation 1002 as described in connection with FIG. 10.

As described in connection with operation 504, the target region corresponding to the lung nodule may be annotated by a bounding box. The processing device 140A may determine whether the lung nodule is a candidate perifissural nodule or a non-perifissural nodule based on the bounding box.

In 1102, the processing device 140A (e.g., the generation module 406) may generate a second transformed bounding box by transforming the bounding box that annotates the target region. The second transformed bounding box may be generated as how the first transformed bounding box is generated as described in connection with operation 902.

In 1104, the processing device 140A (e.g., the generation module 406) may segment, from the second segmentation image, a second region corresponding to the second transformed bounding box.

In some embodiments, the processing device 140A may determine or obtain feature information of the second transformed bounding box. The feature information of the second transformed bounding box may include a shape, a size, a position (e.g., a coordinate of the center point in a coordinate system, such as a world coordinate system), or the like, or any combination thereof, of the second transformed bounding box. The processing device 140A may segment the second region corresponding to the second transformed bounding box from the second segmentation image based on the feature information of the second transformed bounding box. For example, the size of the second region may be equal to the second transformed bounding box. Additionally or alternatively, the position of the center point of the second region (e.g., represented as a coordinate in the world coordinate system) may be the same as that of the second transformed bounding box.

In 1106, the processing device 140A (e.g., the generation module 406) may determine, based on the segmented second region, whether the lung nodule is a candidate perifissural nodule or a non-perifissural nodule.

In some embodiments, the second region may include one or more image elements (e.g., pixels or voxels) corresponding to different lung lobes of the subject. For example, the processing device 140A may determine a fourth ratio relating to the count of the image elements of the different lung lobes. The fourth ratio may include a ratio of the count of the image elements of the upper lobe of the left lung to a count of the image elements of the lower lobe of the left lung, a ratio of the count of the image elements of the upper lobe of the right lung to the count of the image elements of the middle lobe of the right lung, a ratio of the count of the image elements of the middle lobe of the right lung to the count of the image elements of the lower lobe of the right lung, or the like, or any combination thereof. The processing device 140A may further determine whether the lung nodule is a candidate perifissural nodule or a non-perifissural nodule based on the fourth ratio. Merely by way of example, if the fourth ratio is within a range from a fourth threshold ratio to a fifth threshold ratio, the processing device 140A may determine that the lung nodule is a candidate perifissural nodule; if the fourth ratio is out of the range from the fourth threshold ratio to the fifth threshold ratio, the processing device 140A may determine that the lung nodule is a non-perifissural nodule.

In some embodiments, the fourth threshold ratio and the fifth threshold ratio may be set by a user, or according to a default setting of the imaging system 100, or determined by the processing device 140A according to an actual need. For example, for each sample image of a sample perifissural nodule, a sample second region may be determined in a similar manner as how the second region corresponding to the target region is determined. The fourth threshold ratio and/or the fifth threshold ratio may be determined based on the sample second regions. Merely by way of example, for each sample second region, the processing device 140A may determine a ratio of the count of the image elements corresponding to the upper lobe of the left lung to the count of the image elements corresponding to the lower lobe of the left lung in the sample second region. The processing device 140A may further determine the fourth threshold ratio and the fifth threshold ratio based on the ratio corresponding to each sample second region.

In some embodiments, the process 1000 and/or the process 1100 may include one or more additional operations. Additionally or alternatively, one or more operations of the process 1000 and/or the process 1100 described above may be omitted. For example, operation 1002 may be omitted, and the processing device 140A may merely perform operation 1004. As another example, operation 1004 may be omitted. In 1002, the processing device 140A may determine whether the lung nodule is a perifissural nodule or a non-perifissural nodule based on the fourth ratio as aforementioned.

Figure 12:
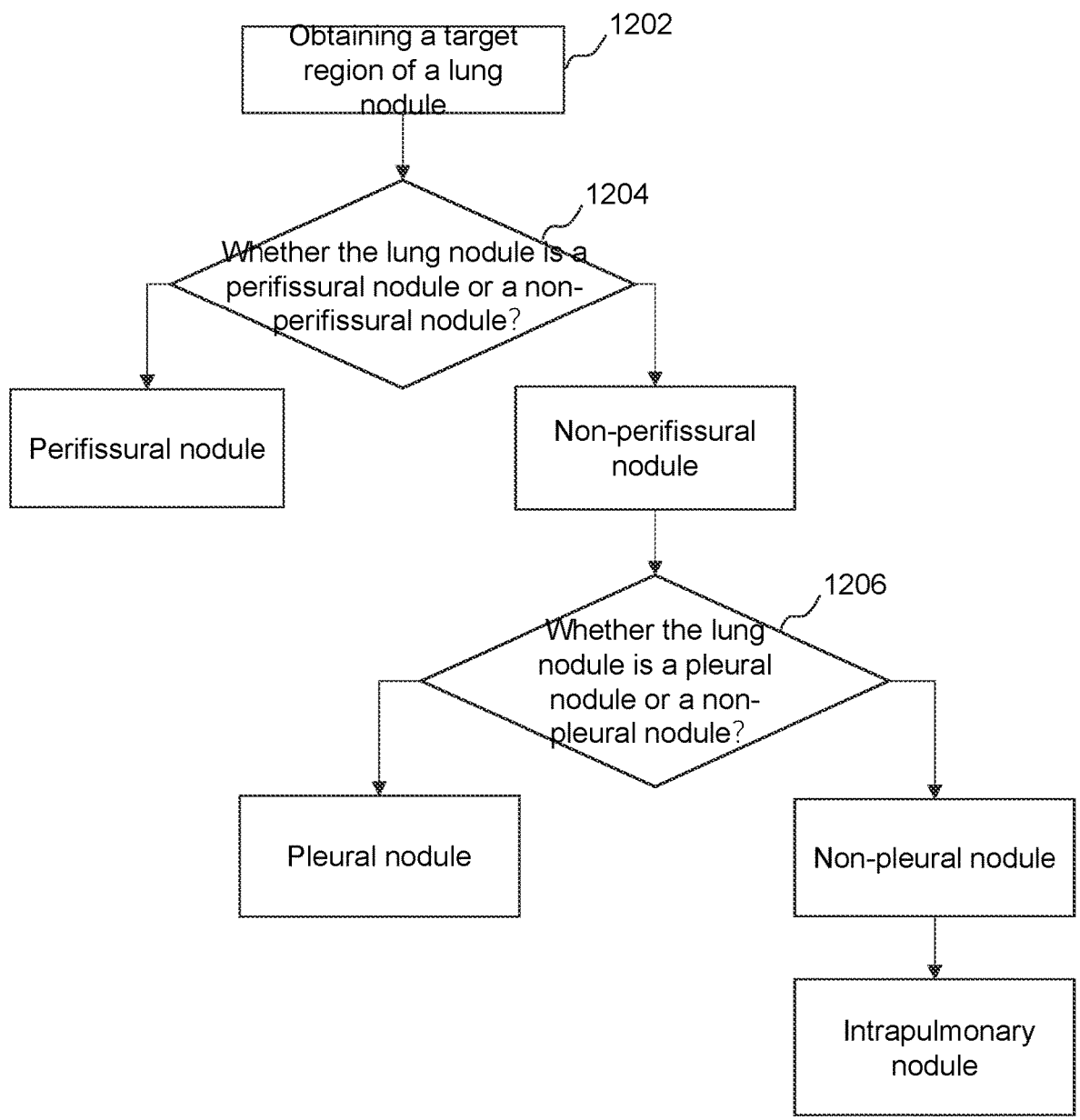
FIG. 12 is a flowchart illustrating an exemplary process for determining a classification relating to a position of a lung nodule according to some embodiments of the present disclosure.

FIG. 12 is a flowchart illustrating an exemplary process for determining a classification relating to a position of a lung nodule according to some embodiments of the present disclosure. In some embodiments, one or more operations of the process 1200 may be performed to achieve at least part of operation 606 as described in connection with FIG. 6.

In 1202, the processing device 140A (e.g., the acquisition module 402) may obtain a target region of a lung nodule.

In some embodiments, the target region may be obtained by performing operation 504 as described in connection with FIG. 5.

In 1204, the processing device 140A (e.g., the generation module 406) may determine whether the lung nodule is a perifissural nodule or a non-perifissural nodule based on the second segmentation image and the target region corresponding to the lung nodule. Operation 1204 may be performed in a similar manner as operation 706 as described in connection with FIG. 7, and the descriptions thereof are not repeated here.

In response to determining that the lung nodule is a non-perifissural nodule, the processing device 140A may proceed to operation 1206.

In 1206, the processing device 140A (e.g., the generation module 406) may determine whether the lung nodule is a pleural nodule or a non-pleural nodule based on the first segmentation image and the target region corresponding to the lung nodule. Operation 1206 may be performed in a similar manner as operation 704 as described in connection with FIG. 7, and the descriptions thereof are not repeated here.

In response to determining that the lung nodule is a non-pleural nodule, the processing device 140A may determine that the lung nodule is an intrapulmonary nodule.

Figure 18:
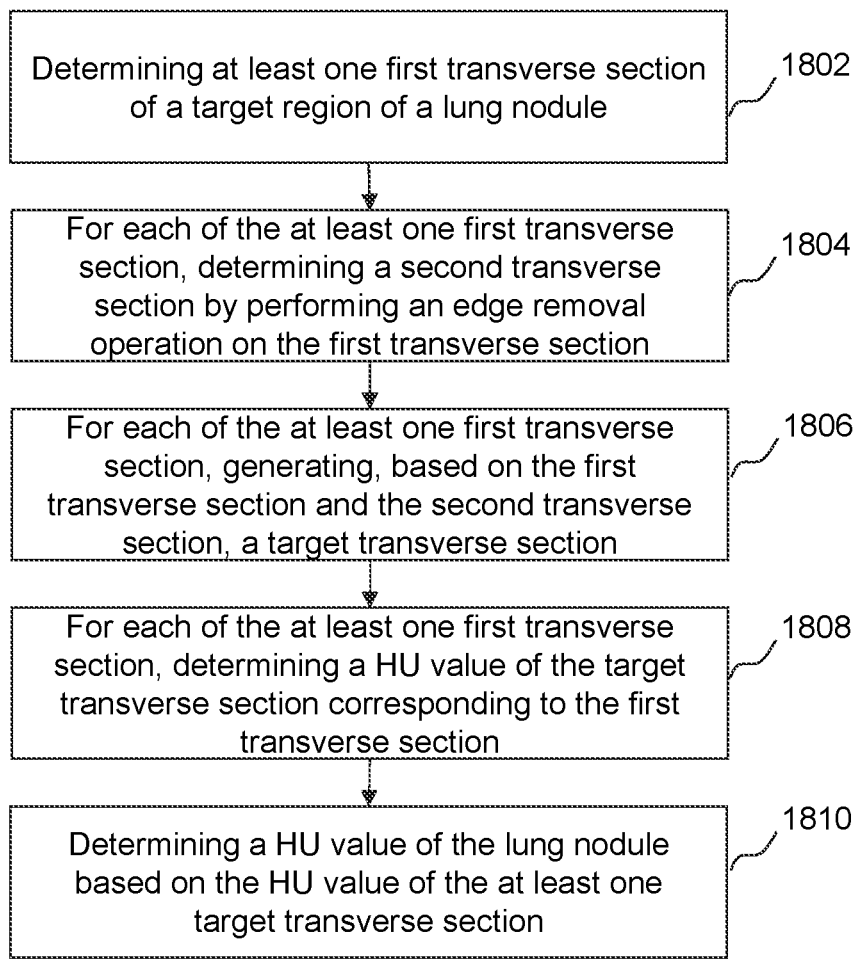
FIG. 18 is a flowchart illustrating an exemplary process for determining a HU value of a lung nodule according to some embodiments of the present disclosure.

FIG. 18 is a flowchart illustrating an exemplary process for determining a HU value of a lung nodule according to some embodiments of the present disclosure. In some embodiments, one or more operations of the process 1800 may be performed to achieve at least part of operation 510 as described in connection with FIG. 5.

In 1802, the processing device 140A (e.g., the generation module 406) may determine at least one first transverse section of a target region of the lung nodule.

The target region may include 3-dimensional image data. In some embodiments, the at least one first transverse section may include transverse section(s) randomly extracted from the target region. Alternatively, the at least one first transverse section may be extracted from the target region according to a specific rule. In some embodiments, the processing device 140A may identify a plurality of candidate transverse sections of the target region, and select the at least one first transverse section from the candidate transverse sections. Merely by way example, the processing device 140A may determine an area of each of the plurality of candidate transverse sections of the target region. The processing device 140A may select, among the plurality of candidate transverse sections, a first candidate transverse section that has the largest area. The processing device 140A may further designate the first candidate transverse section as one of the at least one first transverse section. Additionally or alternatively, the processing device 140A may select, among the plurality of candidate transverse sections, one or more second candidate transverse sections within a predetermined distance with respect to the first candidate transverse section. The processing device 140A may further designate each of the one or more second candidate transverse sections as one of the at least one first transverse section.

Figure 20:
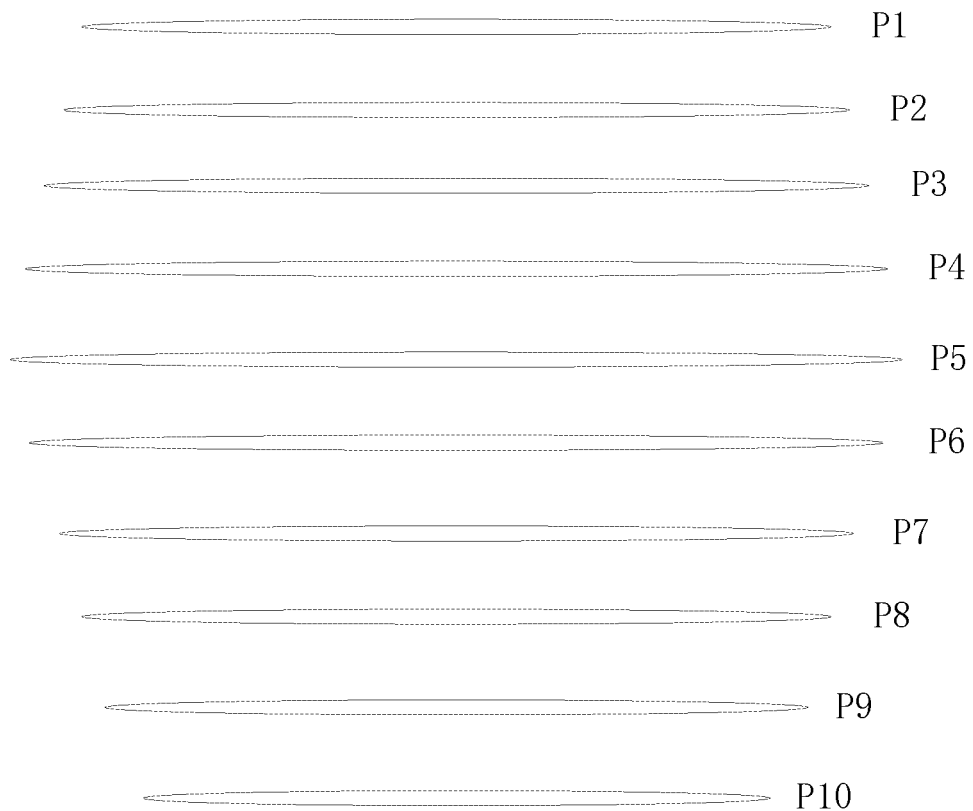
FIG. 20 is a schematic diagram illustrating multiple exemplary candidate transverse sections of a lung nodule according to some embodiments of the present disclosure.

Merely by way of example, FIG. 20 is a schematic diagram illustrating multiple exemplary candidate transverse sections of a lung nodule according to some embodiments of the present disclosure. As shown in FIG. 20, the lung nodule has ten candidate transverse sections P1 to P10, among which the candidate transverse section P5 has the largest area. The candidate transverse section P5 may be determined as a first candidate transverse section of the lung nodule. Additionally or alternatively, one or more candidate transverse sections each of which is within a predetermined distance (e.g., two transverse sections) with respect to the candidate transverse section P5 may be determined as second candidate transverse section(s), that is, the processing device 140A may determine the candidate transverse sections P3, P4, P6, and P7 as second candidate transverse sections. The processing device 140A may further determine the candidate transverse sections P3, P4, P5, P6, and P7 as first transverse sections of the lung nodule.

In 1804, for each of the at least one first transverse section, the processing device 140A (e.g., the generation module 406) may determine a second transverse section by performing an edge removal operation on the first transverse section.

The edge area of a first transverse section may affect the determination accuracy of the HU value of the lung nodule. For example, when the edge area of the first transverse section includes halo, the HU value of the lung nodule determined based on the first transverse section may be inaccurate. Thereby, the processing device 140A may determine a second transverse section by performing an edge removal operation on each first transverse section to reduce or eliminate the effect of the edge area of each first transverse section.

In some embodiments, the processing device 140A may perform an edge removal operation on a first transverse section by an image erosion operation. An image erosion operation may be performed by processing each pixel in an image using a structuring element, and determining a new pixel value of each pixel based on the structuring element and pixel value(s) of pixel(s) covered by the structuring element.

Figure 21:
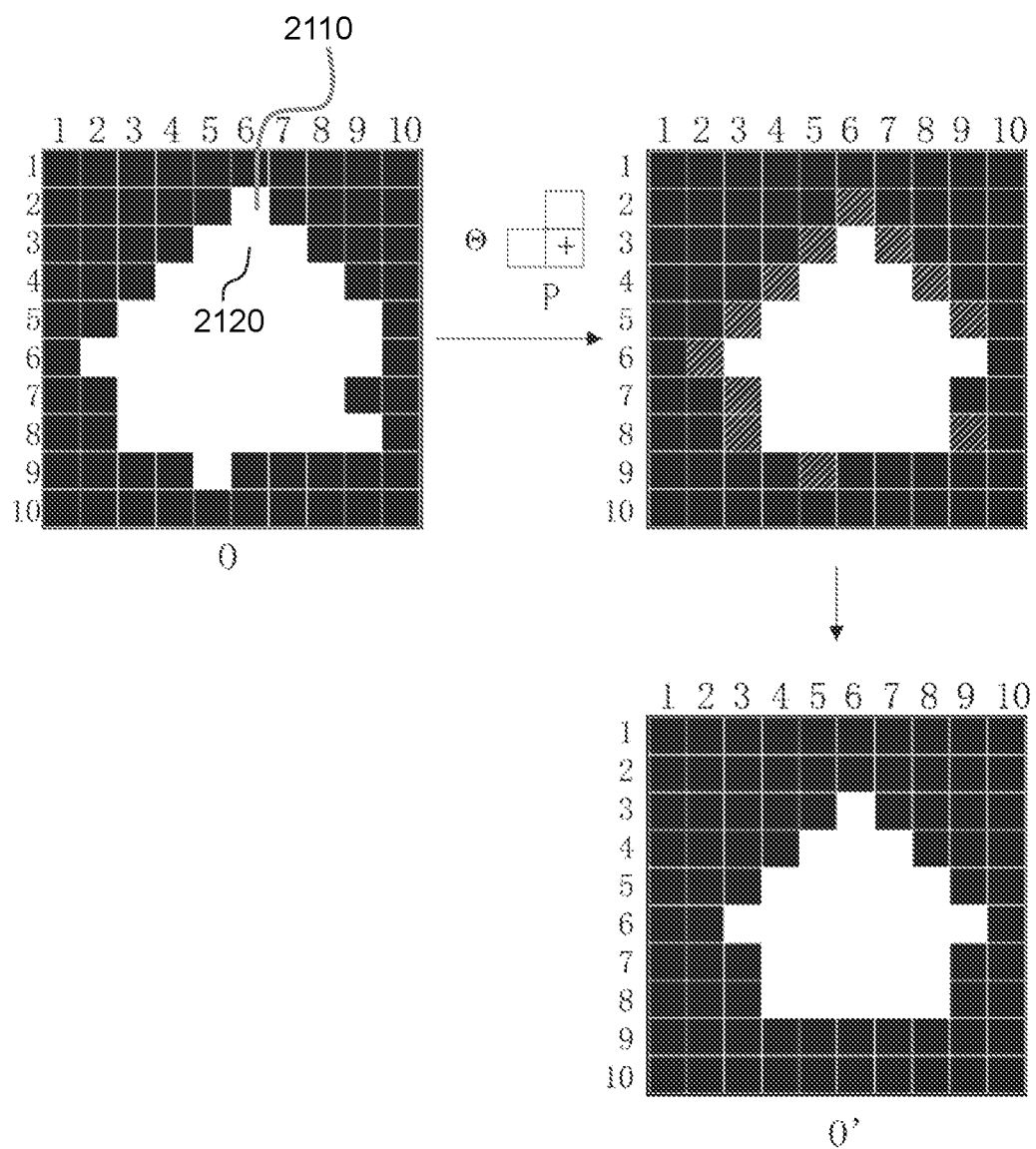
FIG. 21 is a schematic diagram illustrating an exemplary process for an image erosion operation according to some embodiments of the present disclosure.

Merely by way of example, FIG. 21 is a schematic diagram illustrating an exemplary process for an image erosion operation according to some embodiments of the present disclosure. As shown in FIG. 20, an image O is a first transverse section to be eroded. Each block in the image O represents a pixel, wherein the pixel value a white block is 1, and the pixel value of a black block is 0. ⊖ represents to an image erosion operation performed on the image O using a structuring element P. A block marked with "+" in the structuring element P is the core of the structuring element P. When processing the image O using the structuring element P, the core of the structuring element P may be placed on each pixel of the image O. If the core of the structuring element P is placed on a certain pixel, and the pixel values of the pixels covered by the structuring element P are all equal to 1, the pixel value of the certain pixel may be still 1; if the pixel values of the pixels covered by the structuring element P are not all equal to 1, the pixel value of the certain pixel may be updated as 0. For example, when the core of the structuring element P is located at a pixel 2110 whose coordinate is [6,2], the structuring element P may also cover a first pixel whose coordinate is [6,1] and a second pixel whose coordinate is [5,2]. Since the pixel values of the first pixel and the second pixel are both equal to 0, the pixel value of the pixel 2110 may be updated as 0. When the core of structuring element P is located at a pixel 2120 whose coordinate is [6,3], the structuring element P may also cover a third pixel whose coordinate is [6,2] and a fourth pixel whose coordinate is [5,3]. Since the pixel values of the pixel 2120, the third pixel, and the fourth pixel are all equal to 1, the pixel value of the pixel 2120 is still equal to 1. The processing device 140A may generate an image O' by performing each pixel of the image O using the structuring element P. In some embodiments, the structuring element P provided in FIG. 20 is merely for illustration purposes, and the shape and/or size of the structuring element P may be modified.

In some embodiments, the processing device 140A may perform an edge removal operation on a first transverse section by performing an operation other than an image erosion operation. For example, the processing device 140A may draw a circle, wherein the center of the circle may coincident with the center point of the first transverse section. The processing device 140A may then designate the area inside the circle as the second transverse section and the area outside the circle as an edge area. As another example, the processing device 140A may draw a closed pattern having another shape (e.g., an ellipse) in the first transverse section, and designate the area inside the closed pattern as the second transverse section.

In 1806, for each of the at least one first transverse section, the processing device 140A (e.g., the generation module 406) may generate a target transverse section based on the first transverse section and the second transverse section.

For example, for a first transverse section, the processing device 140A may determine a ratio of a size of the second transverse section to a size of the first transverse section. The processing device 140A may generate a comparison result by comparing the ratio with a first threshold and a second threshold. The second threshold is greater than the first threshold. The first threshold and/or second threshold may be set by a user, or according to a default setting of the imaging system 100, or determined by the processing device 140A according to an actual need. For example, the first threshold may be equal to 0.3, 0.35, or the like. The second threshold may be equal to 0.6, 0.65, or the like. The processing device 140A may further generate the target transverse section based on the comparison result, and one of the first transverse section and the second transverse section. More descriptions for generating a target transverse section may be found elsewhere in the present disclosure (e.g., FIG. 19 and the descriptions thereof).

In 1808, for each of the at least one first transverse section, the processing device 140A (e.g., the generation module 406) may determine a HU value of the corresponding target transverse section.

For example, for a target transverse section, a HU value of each of a plurality of pixels of the target transverse section may be determined, and the HU value of the target transverse section may be an average value or a maximum value of the HU values of the pixels of the target transverse section. In some embodiments, the processing device 140A may send the target transverse section to another computing device (e.g., an image processing device of a third party), and then receive the HU value of the target transverse section from the computing device.

In 1810, the processing device 140A (e.g., the generation module 406) may determine the HU value of the lung nodule based on the HU value of the at least one target transverse section.

In some embodiments, if there is only one target transverse section, the processing device 140A may determine the HU value of the target transverse section as the HU value of the lung nodule. If there are a plurality of target transverse sections, the processing device 140A may determine an average value (e.g., an arithmetic mean value or a weight mean value) of the HU values of the plurality of target transverse sections, and designate the average value as the HU value of the lung nodule. In some embodiments of the present disclosure, the HU value of the lung nodule may be determined based on the first transverse section that has the largest area and also one or more transverse sections adjacent to the first transverse section with the largest area. This may improve the accuracy of the determined HU value of the lung nodule.

Figure 19:
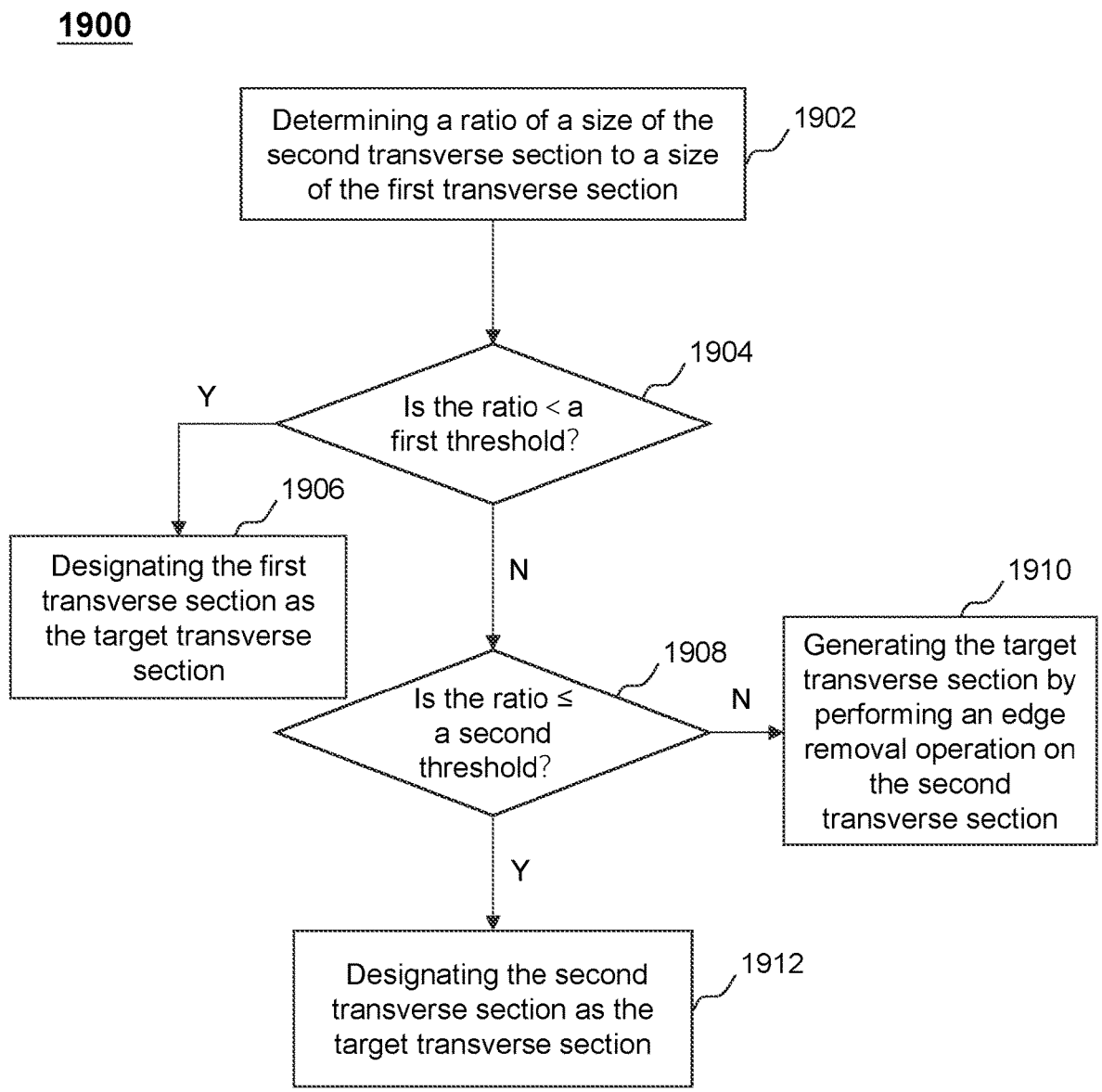
FIG. 19 is a flowchart illustrating an exemplary process for determining a target transverse section based on a first transverse section and a second transverse section according to some embodiments of the present disclosure.

FIG. 19 is a flowchart illustrating an exemplary process for determining a target transverse section based on a first transverse section and a second transverse section according to some embodiments of the present disclosure. In some embodiments, one or more operations of the process 1900 may be performed to achieve at least part of operation 1806 as described in connection with FIG. 18.

In 1902, the processing device 140A (e.g., the generation module 406) may determine a ratio of a size of the second transverse section to a size of the first transverse section. For example, the size of a transverse section may be measured by an area and/or a diameter of the transverse section.

In 1904, the processing device 140A (e.g., the generation module 406) may determine whether the ratio is smaller than the first threshold.

In response to determining the ratio is smaller than the first threshold, the process 1900 may proceed to operation 1906, in which the processing device 140A (e.g., the generation module 406) may designate the first transverse section as the target transverse section. A ratio smaller than the first threshold may suggest that the edge area removed from the first transverse section is too large (e.g., the size of the edge area is greater than a first size) and the size of the second transverse section is too small (e.g., the size of the second transverse section is below a second size), wherein the first size and the second size may be the same or different. The HU value of the lung nodule determined based on such a second transverse section may have a reduced accuracy, and the small size of the second transverse section may have a greater impact on the determination accuracy of the HU value than the edge area of the first transverse section. Therefore, if the ratio is smaller than the first threshold, the processing device 140A may designate the original first transverse section as the target transverse section.

In response to determining the ratio is greater than or equal to the first threshold, the process 1900 may proceed to operation 1908, in which the processing device 140A (e.g., the generation module 406) may determine whether the ratio is smaller than or equal to the second threshold.

In response to determining the ratio is smaller than or equal to the second threshold, the process 1900 may proceed to operation 1912, in which the processing device 140A (e.g., the generation module 406) may designate the second transverse section as the target transverse section. A ratio greater than or equal to the first threshold and smaller than or equal to the second threshold may suggest that the edge area removed from the first transverse section and the second transverse section have appropriate sizes. Therefore, the HU value of the lung nodule may be determined based on the second transverse section to eliminate or reduce the influence of the edge area of the lung nodule.

In response to determining the ratio is greater than the second threshold, the process 1900 may proceed to operation 1910, in which the processing device 140A (e.g., the generation module 406) may generate the target transverse section by performing an edge removal operation on the second transverse section. For example, the second transverse section may be regarded as an updated first transverse section, and the processing device 140A may perform an edge removal operation on the updated first transverse section (i.e., the second transverse section) to generate an updated second transverse section. The processing device 140A may further determine an updated ratio of the size of the updated second transverse section to the size of the updated first transverse section. Operations 1902 to 1912 (or a portion thereof) may be performed iteratively until the updated ratio is smaller than or equal to the second threshold in a certain iteration.

In some embodiments, the edge removal operation may produce different processing effects on different first transverse sections. Merely by way of example, the size of the second transverse section may be too small if the edge area removed by the edge removal operation is too large, and the size of the second transverse section may be too large if the edge area removed by the edge removal operation is too small. In such cases, the target transverse section and the HU value of the lung nodule determined based on the second transverse section may have reduced accuracy. In the process 1900, a ratio of the size of the second transverse section to a size of the first transverse section may be determined and serve as a basis of the determination of the target transverse section. By introducing the ratio, the process effect of the edge removal operation may be taken into consideration in the determination of the target transverse section, which may improve the accuracy of the HU value of the lung nodule determined based on the target transverse section.

According to some embodiments of the present disclosure, the area of a plurality of candidate transverse sections of a target region of a lung nodule may be determined, and one or more first transverse sections each having a relatively large area may be selected from the candidate transverse sections. An edge removal operation may be performed on each first transverse section to generate a second transverse section, so as to reduce or eliminate the effect of the edge area of the first transverse section. For each first transverse section, a target transverse section may further be determined based on a ratio of a size of the second transverse section to a size of the first transverse section. The HU value of the lung nodule may be determined based on the target transverse section corresponding to each first transverse section. Conventionally, a user needs to manually identify a transverse section of the lung nodule having the largest area, and the HU value of the lung nodule may be determined based on the transverse section identified by the user. Compared with the conventional approach for HU value determination, the systems and methods for HU value determination disclosed herein may be fully or partially automated, more accurate and efficient by, e.g., reducing the workload of the user, cross-user variations, and the time needed for the HU value determination.

Figure 22:
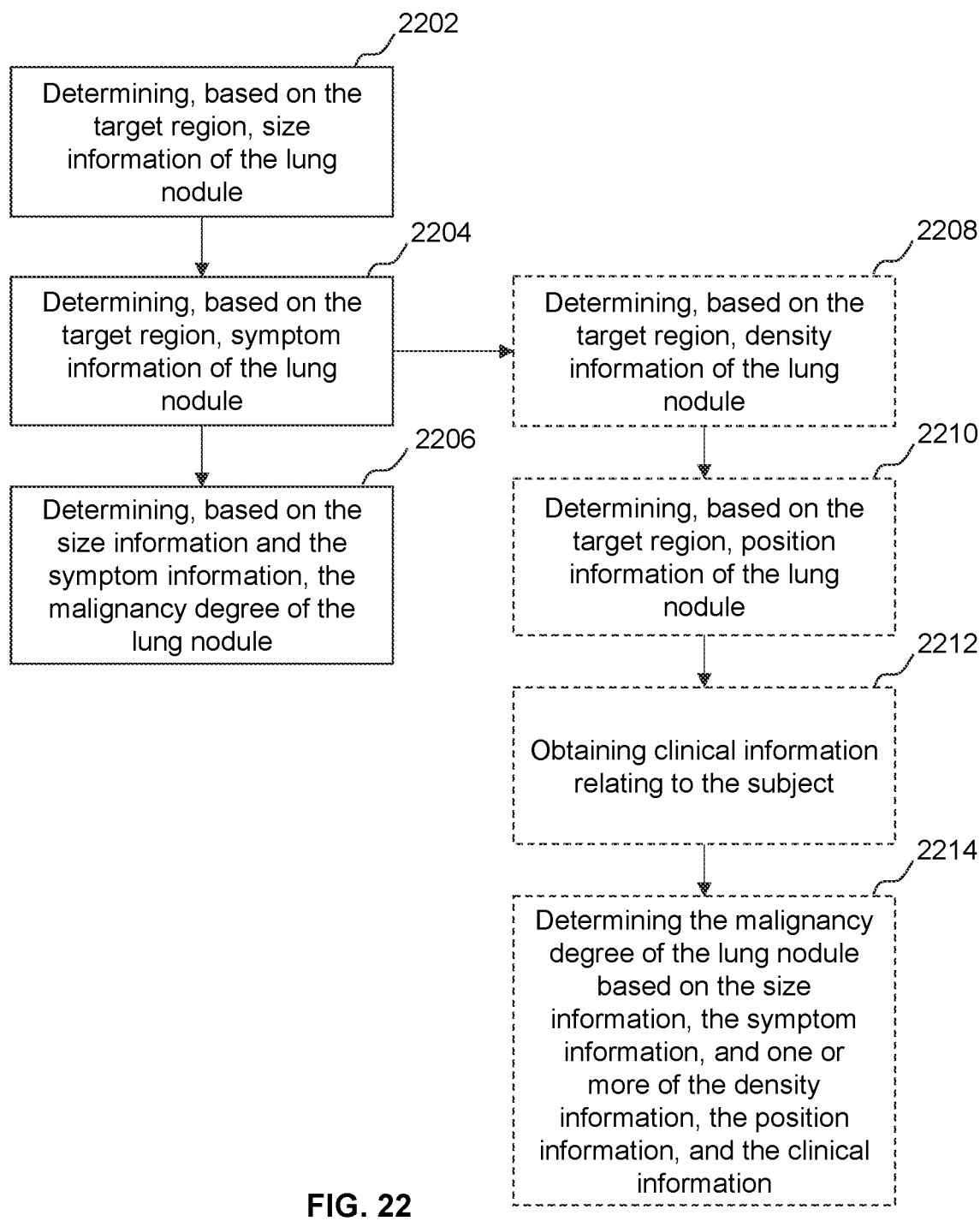
FIG. 22 is a flowchart illustrating an exemplary process for determining a malignancy degree of a lung nodule according to some embodiments of the present disclosure.

FIG. 22 is a flowchart illustrating an exemplary process for determining a malignancy degree of a lung nodule according to some embodiments of the present disclosure. In some embodiments, one or more operations of the process 2200 may be performed to achieve at least part of operation 512 as described in connection with FIG. 5.

In 2202, the processing device 140A (e.g., the generation module 406) may determine size information of the lung nodule based on the target region.

In some embodiments, the target region may include 3-dimensional image data. The size information of the lung nodule may include a volume, a maximum inner diameter of the lung nodule, a maximum diameter in of a plurality of cross sections of the lung nodule, or the like, or any combination thereof. Alternatively, the target region may include 2-dimensional image data, and the size information of the lung nodule may include an area, a perimeter, a diameter, or the like, or any combination thereof, of the lung nodule. In some embodiments, as described in connection with FIG. 5, the target region of the lung nodule may be represented as a segmentation mask of the lung nodule. The size information may be determined based on the segmentation mask.

In 2204, the processing device 140A (e.g., the generation module 406) may determine symptom information of the lung nodule based on the target region.

As used herein, symptom information of a lung nodule refers to information relating to a symptom that may indicate a condition of the lung nodule, for example, indicate whether the lung nodule is benign or malignant. For example, the symptom information of a lung nodule may include information relating to a benign symptom and/or information relating to a malignant symptom. The benign symptom may indicate that the lung nodule is benign. Exemplary benign symptoms may include that the lung nodule is classified as a calcified nodule according to its density information, the lung nodule has adipose tissue, the lung nodule is located at the pleura or the fissure, etc. The malignant symptom may indicate that the lung nodule is malignant. Exemplary malignant symptoms may include that the lung nodule has one or more of a lobulation, a speculation, a pleural traction, an air bronchogram, a vacuole disease, and an eccentric thick-walled cavity, or the like, or any combination thereof.

In some embodiments, the symptom information may be determined manually by a user. For example, the target region may be displayed on a terminal device, and the user may input or select one or more benign symptoms and/or malignant symptoms that the lung nodule has via the terminal device. Alternatively, the symptom information may be determined by the processing device 140A by analyzing the target region. For example, the symptom information may be determined based on the target region using a symptom determination model (e.g., a classification model). The symptom determination model may be configured to receive image data of a lung nodule as an input, and output information relating to symptom(s) that the lung nodule has. For example, the symptom determination model may output a determination result of whether the lung nodule has one or more specific symptoms and/or a probability that the lung nodule has the specific symptom(s). In some embodiments, the symptom determination model may be trained according to a supervised learning algorithm by the processing device 140B or another computing device (e.g., a processing device of a vendor of the symptom determination model). In some embodiments, a plurality of symptom determination models, each of which is configured to detect one or more specific symptoms, may be used.

In some embodiments, after the size information and the symptom information are determined, the processing device 140A may perform operation 2206 to determine the malignancy degree of the lung nodule based on the size information and the symptom information. Alternatively, the processing device 140A may further determine additional information relating to the lung nodule, and determine the malignant degree of the lung nodule based on a combination of the size information, the symptom information, and the additional information. For example, the processing device 140A may perform operations 2208-2214 to determine the malignancy degree of the lung nodule.

In 2206, the processing device 140A (e.g., the generation module 406) may determine the malignancy degree of the lung nodule based on the size information and the symptom information.

As used herein, the malignancy degree of a lung nodule may reflect a probability that the lung nodule is malignant (e.g., a malignant cancer). In some embodiments, the malignant degree of the lung nodule may be represented in various forms. For example, the malignant degree may be represented as a score, and a greater score may indicate a higher probability that the lung nodule is malignant. As another example, the malignant degree may include a low-risk degree, a moderate-risk degree, and a high-risk degree. Merely by way of example, if the size of the lung nodule is less than a certain value (e.g., the maximum diameter of the cross sections of the lung nodule is less than 5 mm) and the lung nodule doesn't have malignant symptoms, the processing device 140A may determine that the malignancy degree of the lung nodule is a low-risk degree. If the size of a lung nodule is within a certain range (e.g., the maximum diameter of the cross sections of the lung nodule is greater than 5 mm and less than 10 mm) and the lung nodule doesn't have malignant symptoms, the processing device 140A may determine that the malignancy degree of the lung nodule is a moderate-risk degree. If the size of a lung nodule is greater than a certain value (e.g., the maximum diameter of cross sections of the lung nodule is greater than 10 mm) and/or the lung nodule has one or more malignant symptoms, the processing device 140A may determine that the malignancy degree of the lung nodule is a high-risk degree.

In 2208, the processing device 140A (e.g., the generation module 406) may determine density information of the lung nodule based on the target region.

For example, the density information of the lung nodule may include a density value (e.g., an average density) of the lung nodule and/or a type of the lung nodule relating to the density of the lung nodule. Merely by way of example, according to the density of the lung nodule, the lung nodule may be classified as one of a solid nodule, a part-solid nodule, a ground-glass nodule, a calcified nodule, etc. A solid nodule refers to a lung nodule that has a similar density to soft tissues of humans. A part-solid nodule refers to a lung nodule that has both a fuzzy part and a high-density part (e.g., a part having a density higher than a threshold density). A ground-glass nodule refers to a lung nodule that is fuzzy and translucent within the lung(s) of the subject. A calcified nodule refers to a lung nodule that is calcified.

In some embodiments, the processing device 140A may send the target region of the lung nodule to another computing device (e.g., an image processing device of a third party), and then receive the density information of the lung nodule from the computing device. Alternatively, the density information may be determined by the processing device 140A by analyzing the target region. For example, the density information may be determined based on the target region using a density determination model (e.g., a classification model). The density determination model may be configured to receive image data of a lung nodule as an input, and output information relating to the density of the lung nodule. For example, the density determination model may output a determination result of whether the lung nodule is a solid nodule, a part-solid nodule, a ground-glass nodule, or a calcified nodule, etc. In some embodiments, the density determination model may be trained according to a supervised learning algorithm by the processing device 140B or another computing device (e.g., a processing device of a vendor of the density determination model).

In 2210, the processing device 140A (e.g., the generation module 406) may determine position information of the lung nodule based on the target region.

The position information of the lung nodule may include, for example, the position of the lung nodule, a classification relating to the position of the lung nodule, or the like, or any combination thereof. Merely by way of example, the classification relating to the position of the lung nodule may include a pleural nodule, a non-pleural nodule, a perifissural nodule, a non-perifissural nodule, an intrapulmonary nodule, a lung nodule located at the left lung, a lung nodule located at the right lung, a lung nodule located at the upper lobe of the left lung, or the like. In some embodiments, the classification relating to the position of the lung nodule may be determined by performing operation 508 as described in connection with FIG. 5.

In 2212, the processing device 140A (e.g., the generation module 406) may obtain clinical information relating to the subject.

The clinical information relating to the subject may include age information, smoking history, medical history (e.g., historical information of malignant tumor), etc. The smoking history may include whether the subject smokes, smoking time information, smoking amount information, etc. The historical information of malignant tumor may include whether the subject has suffered from a malignant tumor, disease duration information relating to the malignant tumor, the type of the malignant tumor, etc. Generally, the probability that the lung nodule is malignant may increase with the age and/or the smoke duration of the subject. Additionally or alternatively, the probability that the lung nodule is malignant may increase if the subject has suffered from a malignant tumor.

In 2214, the processing device 140A (e.g., the generation module 406) may determine the malignancy degree of the lung nodule based on the size information, the symptom information, and one or more of the density information, the position information, and the clinical information.

In some embodiments, one or more of the density information, the position information, and the clinical information may be used in the determination of the malignant degree of the lung nodule. For example, the processing device 140A may determine the malignant degree based on the size information, the symptom information, and the density information of the lung nodule. More descriptions regarding the determination of the malignant degree based on the size information, the symptom information, and the density information of the lung nodule may be found elsewhere in the present disclosure. See, e.g., operation 2308 and relevant descriptions thereof. As another example, the processing device 140A may determine the malignancy degree of the lung nodule based on the size information, the symptom information, the position information, and the clinical information. More descriptions regarding the determination of the malignancy degree of the lung nodule based on the size information, the symptom information, the position information, and the clinical information may be found elsewhere in the present disclosure. See, e.g., operations 2304-2306 and relevant descriptions thereof.

In some embodiments, the size information, the symptom information, and the density information, the position information, and the clinical information may form a plurality of sets of information. The processing device 140A may determine a malignant degree based on each of the sets of information, and determine a final malignant degree based on the malignant degrees. In this way, the processing device 140A may evaluate the lung nodule from different perspectives based on different information, thereby generating a final malignant degree with an improved accuracy and reliability.

In some embodiments, the malignancy degree of the lung nodule may be determined using a malignancy degree determination model. The malignancy degree determination model may be configured to receive information (e.g., one or more of size information, symptom information, density information, position information, and clinical information) relating to a lung nodule as an input, and output the malignancy degree of the lung nodule.

It should be noted that the above description regarding the process 2200 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 2200 may be accomplished with one or more additional operations not described and/or without one or more of the operations discussed above. For example, one or more of operations 2208 to 2214 may be omitted. As another example, the process 2200 may include an additional operation to obtain additional information relating to the lung nodule, such as environmental information of a residence of the subject, a family history of the subject, etc. The additional information may be used in the determination of the malignant degree of the lung nodule.

Figure 23:
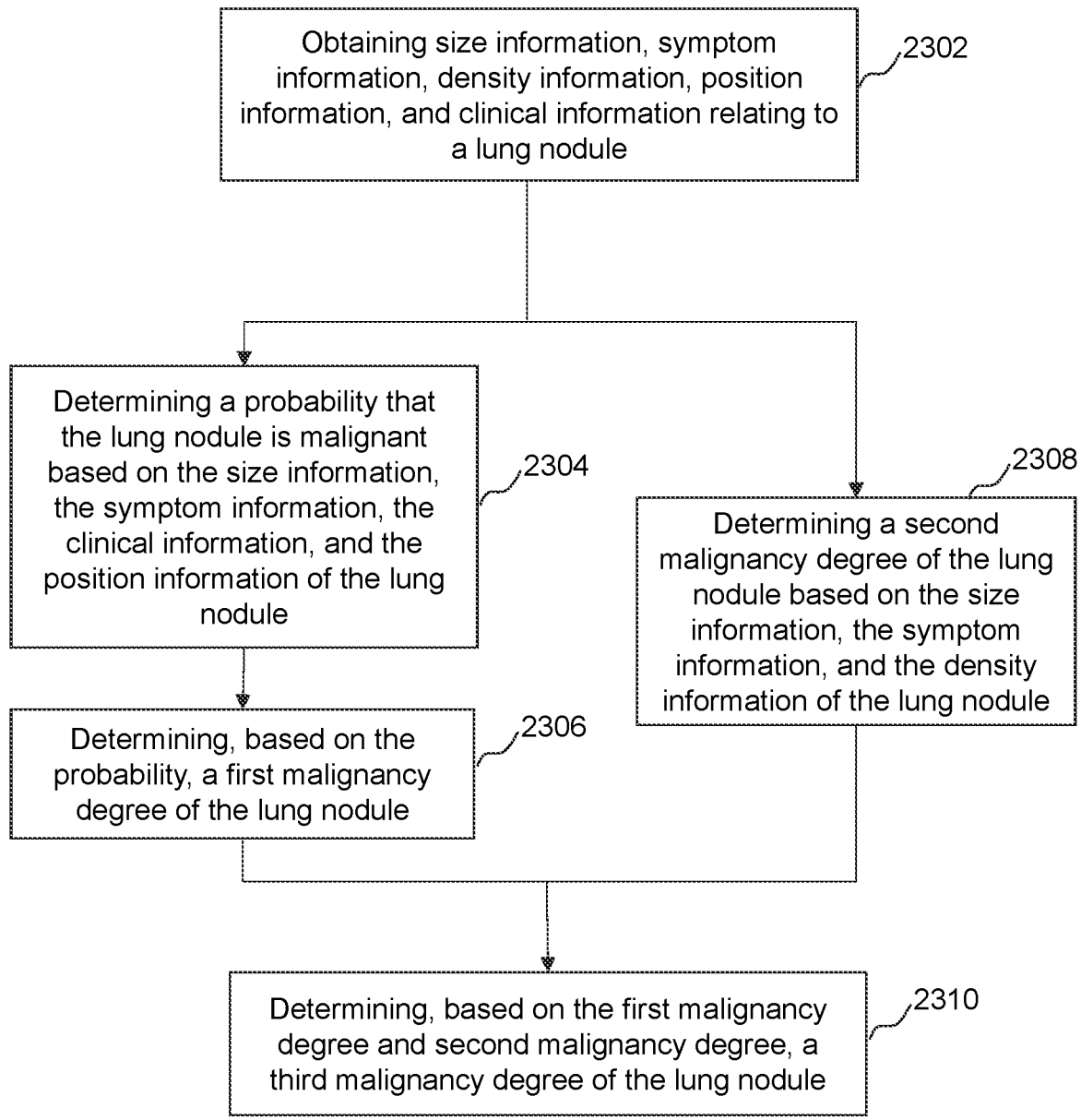
FIG. 23 is a flowchart illustrating an exemplary process for determining a malignancy degree of a lung nodule according to some embodiments of the present disclosure.

FIG. 23 is a flowchart illustrating an exemplary process for determining a malignancy degree of a lung nodule according to some embodiments of the present disclosure. In some embodiments, one or more operations of the process 2300 may be performed to achieve at least part of operation 2214 as described in connection with FIG. 22.

In 2302, the processing device 140A (e.g., the generation module 406) may determine size information, symptom information, density information, position information, and clinical information relating to the lung nodule.

In some embodiments, one or more of the size information, the symptom information, the density information, the position information, and the clinical information may be previously determined and stored in a storage device (e.g., the storage device 150, the storage 220, the storage 390, or an external source). For example, the clinical information may be stored in a medical database, and the processing device 140A may retrieve the clinical information from the storage device. In some embodiments, one or more of the size information, the symptom information, the density information, the clinical information, and the position information may be determined by the processing device 140A based on the target region corresponding to the lung nodule. For example, the size information, the symptom information, the density information, the position information, and the clinical information may be determined by performing operations 2202, 2204, 2208, 2210, and 2212 as described in connection with FIG. 22, respectively.

In 2304, the processing device 140A (e.g., the generation module 406) may determine a probability that the lung nodule is malignant based on the size information, the symptom information, the clinical information, and the position information of the lung nodule.

In some embodiments, the processing device 140A may determine a weighted sum of the size information, the symptom information, the clinical information, and the position information of the lung nodule. The processing device 140A may further determine the probability that the lung nodule is malignant based on the weighted sum. Merely by way of example, the probability that the lung nodule is malignant may be determined according to Equation (1) and Equation (2) as below:

$$x = m + A*a\% + B*b\% + C*c\% + D*d\% + E*e\% + F*f\%, \quad (1)$$

$$P = \frac{e^x}{1+e^x}, \quad (2)$$

where x denotes the weighted sum, m denotes a constant term; A denotes the age of the subject, B denotes a parameter value relating to the smoking history of the subject, C denotes a parameter value relating to the medical history of the subject, D denotes a parameter value relating to the size information of the lung nodule, E denotes a parameter value relating to the symptom information of the lung nodule, F denotes a parameter value relating to the position information of the lung nodule, a % denotes a weight of the age, b % denotes a weight of the smoking history, c % denotes a weight of the medical history, d % denotes a weight of the size information, e % denotes a weight of the symptom information, f % denotes a weight of the position information, and P denotes the probability that the lung nodule is malignant.

In some embodiments, components of Equations (1) and (2), such as the constant term, a weight, a parameter value, may be determined according to a default setting of the imaging system, manually set by a user, or by the processing device 140A according to an actual need. For example, x, A, B, C, D, E, F may be determined according to Equations (3)-(9), respectively $$x = -6.8272 + A*0.0391 + B*0.7919 + \quad (3)$$
$$C*1.3388 + D*0.1274 + E*1.0407 + F*0.7838,$$

$$A = \text{the age of the subject}, \quad (4)$$

$$B = \begin{cases} 1, \text{ the subject smokes} \\ 0, \text{ other} \end{cases}, \quad (5)$$

$$C = \begin{cases} 1, \text{ the subject has suffered from extrathoracic malignant tumor} \\ \quad \text{for more than 5 years} \\ 0, \text{ other} \end{cases}, \quad (6)$$

$$D = \text{the maximum diameter of the cross sections of the lung} \quad (7)$$
$$\text{nodule (mm)},$$

$$E = \begin{cases} 1, \text{ there are burrs on the edge of the lung nodule} \\ 0, \text{ other} \end{cases}, \quad (8)$$

$$F = \begin{cases} 1, \text{ the lung nodule is located at the upper lobe of the right} \\ \quad \text{lung or left lung} \\ 0, \text{ other} \end{cases}. \quad (9)$$

It should be noted that Equations (1)-(9) are merely provided for the purposes of illustration, and not intended to limit the scope of the present disclosure. For persons having ordinary skills in the art, multiple variations and modifications may be made under the teachings of the present disclosure. For example, Equation (1) may include one or more other components, and/or one or more components of Equation (1) as described above may be omitted. As another example, the value of the weight of the smoking history in Equation (3) may be modified.

In 2306, the processing device 140A (e.g., the generation module 406) may determine a first malignancy degree of the lung nodule based on the probability.

For example, if the probability is less than a first probability, the processing device 140A may determine that the first malignancy degree is a low-risk degree. If the probability is greater than or equal to the first probability and less than a second probability, the processing device 140A may determine that the first malignancy degree of the lung nodule is a moderate-risk degree. If the probability is greater than or equal to the second probability, the processing device 140A may determine that the first malignancy degree of the lung nodule is a high-risk degree. The first probability and second probability may be set by a user, or according to a default setting of the imaging system 100, or determined by the processing device 140A according to an actual need. For example, the first probability may be equal to 4%, 5%, or the like, and the second probability may be equal to 64%, 65%, or the like.

In some embodiments, the processing device 140A may designate the first malignancy degree of the lung nodule as the malignancy degree of the lung nodule.

In 2308, the processing device 140A (e.g., the generation module 406) may determine a second malignancy degree of the lung nodule based on the size information, the symptom information, and the density information of the lung nodule.

For example, Table 1 illustrates an exemplary looking-up table for determining a malignant degree of a lung nodule according to some embodiments of the present disclosure. Merely by way of example, according to the first line of Table 1, if the maximum diameter of the cross sections of a solid nodule is greater than 15 mm, the processing device 140A may determine that the malignant degree of the solid nodule is a high-risk degree.

TABLE 1

| Density information | Size information | Symptom information | Malignant degree |
|---|---|---|---|
| solid nodule | the maximum diameter of the cross sections > 15 mm | / | high-risk degree |
| | 8 mm < the maximum diameter of the cross sections < 15 mm | has malignant symptom(s) | high-risk degree |
| | 5 mm < the maximum diameter of the cross sections < 15 mm | doesn't have malignant symptom(s) | moderate-risk degree |
| | the maximum diameter of the cross sections < 5 mm | / | low-risk degree |
| part-solid nodule | the maximum diameter of the cross sections > 8 mm | / | high-risk degree |
| | the maximum diameter of the cross sections ≤ 8 mm | / | moderate-risk degree |
| ground-glass nodule | the maximum diameter of the cross sections > 5 mm | / | moderate-risk degree |
| | the maximum diameter of the cross sections ≤ 5 mm | / | low-risk degree |
| calcified nodule | / | / | low-risk degree |

It should be noted that the examples illustrated in Table. 1 is merely provided for the purposes of illustration, and not intended to limit the scope of the present disclosure. For persons having ordinary skills in the art, multiple variations and modifications may be made under the teachings of the present disclosure. For example, the size information of the lung nodule may include a volume and/or a maximum inner diameter of the lung nodule.

In 2310, the processing device 140A (e.g., the generation module 406) may determine a third malignancy degree (or referred to as a final malignancy degree) of the lung nodule based on the first malignancy degree and second malignancy degree.

For example, the processing device 140A may obtain a first confidence coefficient corresponding to the first malignancy degree and the second confidence coefficient corresponding to the second malignancy degree. The first confidence coefficient and the second confidence coefficient may be set by a user, or according to a default setting of the imaging system 100, or determined by the processing device 140A according to an actual need. For example, the first confidence coefficient may be equal to 90%, and the second confidence coefficient may be equal to 95%. The processing device 140A may further determine the third malignancy degree of the lung nodule based on the first malignancy degree, the second malignancy degree, the first confidence coefficient, and the second confidence coefficient.

According to some embodiments of the present disclosure, various information relating to the lung nodule may be obtained or determined and used in the determination of the malignant degree of the lung nodule. For example, the size, symptom, position, density, and clinical information relating to the lung nodule may be taken into consideration in the determination of the malignant degree of the lung nodule. Conventionally, the malignant degree of the lung nodule may be determined manually by a user (e.g., a doctor) based on an image of the lung nodule according to experience, which may be inaccurate and inefficient. Compared with the conventional approach, the systems and methods for determining a malignant degree of the lung nodule may be implemented without or with reduced or minimal user intervention, which is time-saving, more efficient, and more accurate.

It should be noted that the above description regarding the process 2300 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 2300 may be accomplished with one or more additional operations not described and/or without one or more of the operations discussed above.

It will be apparent to those skilled in the art that various changes and modifications can be made in the present disclosure without departing from the spirit and scope of the disclosure. In this manner, the present disclosure may be intended to include such modifications and variations if the modifications and variations of the present disclosure are within the scope of the appended claims and the equivalents thereof.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate a certain variation (e.g., ±1%, ±5%, ±10%, or ±20%) of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable. In some embodiments, a classification condition used in classification or determination is provided for illustration purposes and modified according to different situations. For example, a classification condition that "a value is greater than the threshold value" may further include or exclude a condition that "the probability value is equal to the threshold value."

What is claimed is:

1. A system for lung nodule evaluation, comprising:
    at least one storage device including a set of instructions; and
    at least one processor configured to communicate with the at least one storage device, wherein when executing the set of instructions, the at least one processor is configured to direct the system to perform operations including:
    obtaining a target image including at least a portion of a lung of a subject;
    segmenting, from the target image, at least one target region each of which corresponds to a lung nodule of the subject; and
    generating an evaluation result with respect to the at least one lung nodule based on the at least one target region, wherein the generating an evaluation result with respect to the at least one lung nodule based on the at least one target region comprises:
        for each of the at least one lung nodule, determining a malignancy degree of the lung nodule based on position information of the lung nodule, wherein the position information includes a classification relating to a position of the lung nodule, and the classification relating to the position of the lung nodule is determined by:
            generating, based on the target image, a first segmentation image and a second segmentation image, wherein the first segmentation image indicates the left lung and the right lung of the subject segmented from the target image, and the second segmentation image indicates at least one lung lobe of the subject segmented from the target image;
            determining whether the lung nodule is a pleural nodule or a non-pleural nodule based on the first segmentation image and the target region corresponding to the lung nodule; and
            in response to determining that the lung nodule is a non-pleural nodule, determining whether the lung nodule is a perifissural nodule or a non-perifissural nodule based on the second segmentation image and the target region corresponding to the lung nodule.

2. The system of claim 1, wherein each of the at least one target region includes 3-dimensional image data, and the generating an evaluation result with respect to the at least one lung nodule based on the at least one target region comprises:
    for each of the at least one lung nodule,
    identifying at least one first transverse section of the target region corresponding to the lung nodule; and
    determining a Hounsfield unit (HU) value of the lung nodule based on the at least one first transverse section of the target region corresponding to the lung nodule.

3. The system of claim 2, wherein the determining a HU value of the lung nodule based on the at least one first transverse section of the target region of the lung nodule comprises:

for each of the at least one first transverse section,
generating a second transverse section by performing an edge removal operation on the first transverse section;
generating, based on the first transverse section and the second transverse section, a target transverse section; and
determining a HU value of the target transverse section; and determining the HU value of the lung nodule based on the HU value of the at least one target transverse section.

4. The system of claim 3, wherein the generating, based on the first transverse section and the second transverse section, a target transverse section comprises:
determining a ratio of a size of the second transverse section to a size of the first transverse section;
generating a comparison result by comparing the ratio with a first threshold and a second threshold, the second threshold being greater than the first threshold; and
generating the target transverse section based on the comparison result, and one of the first transverse section and the second transverse section.

5. The system of claim 1, wherein the determining the classification relating to the position of the lung nodule comprises:
in response to determining that the lung nodule is a non-perifissural nodule, determining that the lung nodule is an intrathoracic nodule.

6. The system of claim 1, wherein the determining a malignancy degree of the lung nodule based on position information of the lung nodule includes:
determining a plurality of sets of information, each set of information including one or more of size information, symptom information, density information, the position information, or clinical information relating to the lung nodule, wherein the size information, the symptom information, the density information, and the position information are determined based on the target region corresponding to the lung nodule
for each set of information, determining a preliminary malignant degree of the lung nodule based on the set of information; and
determining a malignancy degree of the lung nodule based on the preliminary malignant degrees corresponding to the plurality of sets of information.

7. The system of claim 6, wherein one set of the plurality of sets of information includes the size information and the symptom information of the lung nodule, the size information of the lung nodule including one or more of a volume, a maximum inner diameter of the lung nodule, a maximum diameter in of a plurality of cross sections of the lung nodule.

8. The system of claim 6, wherein the symptom information is determined based on the target region using a symptom determination model, an input of the symptom determination model including the target region, and an output of the symptom determination model including a determination result of whether the lung nodule has one or more symptoms and/or a probability that the lung nodule has the one or more symptoms.

9. The system of claim 6, wherein one set of the plurality of sets of information includes the size information, the symptom information, and the density information of the lung nodule.

10. The system of claim 6, wherein the density information of the lung nodule is determined based on the target region using a density determination model, the density information of the lung nodule including a type of the lung nodule relating to a density of the lung nodule, and according to the density of the lung nodule, the lung nodule being classified as one of a solid nodule, a part-solid nodule, a ground-glass nodule, or a calcified nodule.

11. The system of claim 6, wherein one set of the plurality of sets of information includes the size information, the symptom information, and the position information.

12. The system of claim 6, wherein one set of the plurality of sets of information includes the size information, the symptom information, the position information, and the clinical information.

13. The system of claim 12, wherein the preliminary malignancy degree of the lung nodule corresponding to the set of information is determined by:
determining a probability that the lung nodule is malignant based on the size information, the symptom information, the position information, and the clinical information of the lung nodule; and
determining, based on the probability, the preliminary malignancy degree of the lung nodule.

14. The system of claim 12, wherein the preliminary malignancy degree of the lung nodule corresponding to the set of information is determined by:
determining the preliminary malignancy degree of the lung nodule by processing the size information, the symptom information, the position information, and the clinical information of the lung nodule using a malignancy degree determination model.

15. The system of claim 6, wherein the plurality of sets of information includes a first set of information and a second set of information, the first set of information including the size information, the symptom information, the position information, and the clinical information, the second set of information including the size information, the symptom information, and the density information,
the preliminary malignant degrees of the plurality of sets of information include a first malignancy degree of the lung nodule determined based on the first set of information and a second malignancy degree of the lung nodule determined based on the second set of information, and
the malignancy degree of the lung nodule is determined based on the first malignancy degree and the second malignancy degree.

16. The system of claim 6, wherein each of the size information, the symptom information, the density information, the position information, and the clinical information is determined as one set of information among the plurality of sets of information.

17. A method for lung nodule evaluation implemented on a computing device having at least one processor and at least one storage device, the method comprising:
obtaining a target image including at least a portion of a lung of a subject;
segmenting, from the target image, at least one target region each of which corresponds to a lung nodule of the subject; and
generating an evaluation result with respect to the at least one lung nodule based on the at least one target region, wherein the generating an evaluation result with respect to the at least one lung nodule based on the at least one target region comprises:

for each of the at least one lung nodule, determining a malignancy degree of the lung nodule based on position information of the lung nodule, wherein the position information includes a classification relating to a position of the lung nodule, and the classification relating to the position of the lung nodule is determined by:

generating, based on the target image, a first segmentation image and a second segmentation image, wherein the first segmentation image indicates the left lung and the right lung of the subject segmented from the target image, and the second segmentation image indicates at least one lung lobe of the subject segmented from the target image;

determining whether the lung nodule is a pleural nodule or a non-pleural nodule based on the first segmentation image and the target region corresponding to the lung nodule; and in response to determining that the lung nodule is a non-pleural nodule, determining whether the lung nodule is a perifissural nodule or a non-perifissural nodule based on the second segmentation image and the target region corresponding to the lung nodule.

18. A non-transitory computer readable medium, comprising a set of instructions for lung nodule evaluation, wherein when executed by at least one processor, the set of instructions direct the at least one processor to effectuate a method, the method comprising:

obtaining a target image including at least a portion of a lung of a subject;

segmenting, from the target image, at least one target region each of which corresponds to a lung nodule of the subject; and generating an evaluation result with respect to the at least one lung nodule based on the at least one target region, wherein the generating an evaluation result with respect to the at least one lung nodule based on the at least one target region comprises:

for each of the at least one lung nodule, determining a malignancy degree of the lung nodule based on position information of the lung nodule, wherein the position information includes a classification relating to a position of the lung nodule, and the classification relating to the position of the lung nodule is determined by:

generating, based on the target image, a first segmentation image and a second segmentation image, wherein the first segmentation image indicates the left lung and the right lung of the subject segmented from the target image, and the second segmentation image indicates at least one lung lobe of the subject segmented from the target image;

determining whether the lung nodule is a pleural nodule or a non-pleural nodule based on the first segmentation image and the target region corresponding to the lung nodule; and in response to determining that the lung nodule is a non-pleural nodule, determining whether the lung nodule is a perifissural nodule or a non-perifissural nodule based on the second segmentation image and the target region corresponding to the lung nodule.

\* \* \* \* \*